United States Patent [19]

Jendralla

[11] Patent Number: 5,856,540
[45] Date of Patent: Jan. 5, 1999

[54] 2,2'-DISUBTITUTED 1,1'-DIPHOSPHINO-FERROCENES AND 1',2-DISUBSTITUTED 1-PHOSPHINO-FERROCENES, PROCESSES FOR PREPARING THEM, THEIR USE, AND TRANSITION METAL COMPLEXES COMPRISING THEM

[75] Inventor: Joachim-Heiner Jendralla, Frankfurt am Main, Germany

[73] Assignee: Hoechst Aktiengesellschaft, Frankfurt am Main, Germany

[21] Appl. No.: 847,448

[22] Filed: Apr. 24, 1997

[30] Foreign Application Priority Data

Apr. 25, 1996 [DE] Germany ......................... 196 16 521.0
Jan. 29, 1997 [DE] Germany ......................... 197 03 126.9

[51] Int. Cl.$^6$ .................................................. C07F 17/02
[52] U.S. Cl. ................................. 556/21; 556/22; 556/28; 556/136; 556/144
[58] Field of Search ............................... 556/21, 22, 28, 556/136, 144

[56] References Cited

FOREIGN PATENT DOCUMENTS

WO 96/16971  6/1996  WIPO.

OTHER PUBLICATIONS

Tamio Hayashi et al., "A New Chiral Ferrocenylphosphine Ligand with $C_2$ Symmetry: Preparation and Us Palladium–catalysed Asymmetric Cross–Coupling," *J. Chem. Soc., Chem. Commun.*, pp. 495–496 (1989).

Lothar Schwink et al., "A New Practical Asymmetric Synthisis of $C_2$ –Symmetrical 1,1'–Ferrocenyl Diols vi CBS–Reduction," *Tetrahedron Letters*, vol. 37, No. 1, pp. 25–28 (1996).

Nishibayashi, et al., J. Org. Chem., 61:1172–1174 (1996), "Enantioselective ortho–Lithiation of Substituted Ferrocenes".

Tsukazaki, et al., J. Am. Chem. Soc., 118:685–686 (1996), "Direct and Highly Enantioselective Synthesis of Ferrocenes with Planar Chirality by (–) Sparteine–Mediated Lithiation".

Price et al., J. Org. Chem., 59:1961–1962 (1994), "Chiral Base–Mediated Asymmetric Synthesis of Tricarbonyl($\eta^6$–arene)chromium Complexes".

Price, et al., Tetrahedron Let., 35(33):6159–6162 (1994), "A Study of Synthesis and Racemisation of a Chiral Lithiated Tricarbonyl($\eta^6$–anisole)chromium Complex".

Rebiére, et al., Angew. Chem. Int. Ed. Engl., 32(4):568–570 (1993), "Asymmetric Synthesis and Highly Diastereoselective ortho–Lithiation of Ferrocenyl Sulfoxides. Application to the Synthesis of Ferrocenyl Derivatives with Planar Chirality".

Hayashi, et al., J. Am. Chem. Soc., 116(10):4221–4226 (1994), "Optically Active Ruthenoccnylbis(phosphines): New Efficient Chiral Phosphine Ligands for Catalytic Asymmetric Reaction".

Hayashi, et al., Tetrahedron Lett., 21:1871–1874 (1980), "Asymmetric Hydrosilylation of Olefins Catalyzed by a Chiral Ferrocenylphosphine–Palladium Complex. Asymmetric Synthesis of Optically Active Alcohols and Bromides from Olefins".

Hayashi, et al., J. Am. Chem. Soc., 104:180–186 (1982), "Asymmetric Synthesis Catalyzed by Chiral Ferrocenylphosphine–Transition Metal Complexes. 2.$^1$ Nickel and Palladium–Catalyzed Asymmetric Grignard Cross–Coupling".

Cullen, et al. Organometallics, 4:346–351 (1985), "Structures of Three Hydrogenation Catalysts [P—P)Rh(NBD] $CIO_4$ and Some Comparative Rate Studies Where . . .".

Zanetti, et al., Organometallics, 15:860–866 (1996), "Synthesis, Characterization, and Application in Asymmetric Hydrogenation Reactions of Chiral Ruthenium(II) Diphosphine Complexes".

Blaser et al., Chimica OGGI,/chemistry today, pp. 11–16 (1995), Enantioselective Reduction Methods for the C=N Function.

*Primary Examiner*—Porfirio Nazario-Gonzalez
*Attorney, Agent, or Firm*—Finnegan, Henderson, Farabow, Garrett & Dunner, L.L.P.

[57] ABSTRACT

The present invention relates to optically active and racemic $C_2$-symmetric 2,2'-disubstituted 1,1'-diphosphinoferrocenes of the formula Ia, to optically active and racemic asymmetric 1',2-disubstituted 1-phosphino-ferrocenes of the formula Ib and to achiral 2,2'-disubstituted 1,1'-diphosphino-ferrocenes of the formula II, to processes for preparing them, especially in accordance with the principle of asymmetric ortho-lithiation, to their use as ligands for transition metal complexes, to transition metal complexes comprising them, and to the use of the transition metal complexes as catalysts, especially in asymmetric syntheses.

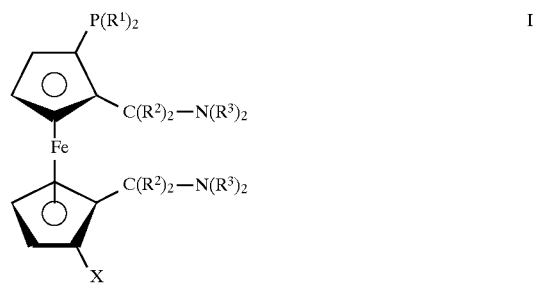

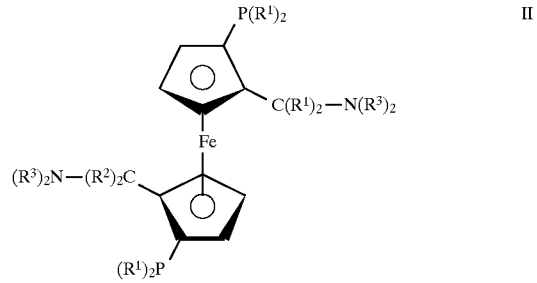

Ia: X = P(R$^1$)$_2$
Ib: X = H

22 Claims, No Drawings

2,2'-DISUBTITUTED 1,1'-DIPHOSPHINO-FERROCENES AND 1',2-DISUBSTITUTED 1-PHOSPHINO-FERROCENES, PROCESSES FOR PREPARING THEM, THEIR USE, AND TRANSITION METAL COMPLEXES COMPRISING THEM

The disclosure of German application 19616521.0 and 19703126.9 filed Apr. 25, 1996 and Jan. 29, 1997 respectively from which the present invention claims priority are hereby incorporated by reference.

The present invention relates to optically active and racemic $C_2$-symmetric 2,2'-disubstituted 1,1'-diphosphino-ferrocenes of the formula Ia, to optically active and racemic asymmetric 1',2-disubstituted 1-phosphino-ferrocenes of the formula Ib and to achiral 2,2'-disubstituted 1,1'-diphosphino-ferrocenes of the formula II, to processes for preparing them, especially in accordance with the principle of asymmetric ortho-lithiation, to their use as ligands for transition metal complexes, to transition metal complexes comprising them, and to the use of the transition metal complexes as catalysts, especially in asymmetric syntheses.

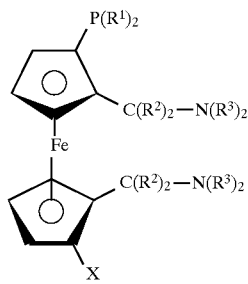

Ia: X = P(R$^1$)$_2$
Ib: X = H

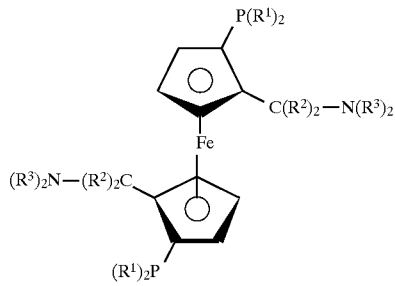

Transition metal complexes of the homochiral, asymmetric mono- and diphosphino-ferrocenes PPFA (formula A) and BPPFA (formula B) (in the formulae, Me is a methyl group and Ph is a phenyl group) bring about high stereoselectivity in asymmetric catalyses if the substrate has a functional group which is able to enter into interactions with the dimethylamino group of the phosphine ligand. Substrates without such functional groups can be reacted with high enantiomer selectivity in asymmetric catalytic reactions if the homochiral $C_2$-symmetric diphosphino-ferrocene of the formula C is employed as ligand (T. Hayashi et al., J. Am. Chem. Soc. 1994, 116, 4221). Despite outstanding results in catalysis, however, the ligands of the formulae A, B and C have not found any notable industrial application, since they are only poorly obtainable. To prepare the optically pure ligands it is necessary in any case to carry out a cleavage of the racemate and also, in the synthesis of the compounds of the formula C, a complex separation of the chiral $C_2$-symmetric C from its achiral meso isomer. There is therefore a need for simple preparation processes and for simple ligands which are easy to obtain.

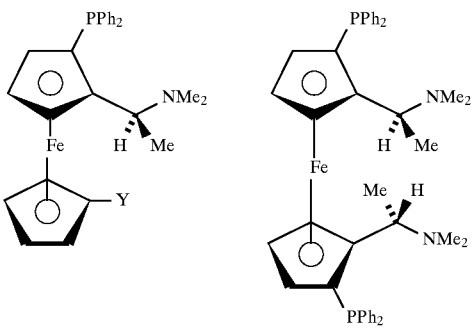

A Y = H; "PPFA"
B Y = PPh$_2$; "BPPFA"
C

In very recent times it has been attempted to obtain homochiral phosphino-ferrocenes by asymmetric ortho-lithiation of substituted ferrocenes by means of homochiral lithium bases. For instance, the dimethylaminomethyl ferrocene of the formula D was diphenylphosphinylated in a yield of 49% and with up to 62% ee (enantiomeric excess) to form the compound of the formula F, by means of 1.5 equivalents of n-butyllithium (n-BuLi) in the presence of 2.0 equivalents of the diamine of the formula E and using from 1.5 to 3.0 equivalents of chlorodiphenylphosphine (Y. Nishibayashi et al., J. Org. Chem. 1996, 61, 1172). Also, the N,N-diisopropylferrocenecarboxamide of the formula G was diphenylphosphinylated in a yield of 82% and with 90% ee to form the compound of the formula J, by means of 2.2 equivalents of n-BuLi and 2.2 equivalents of the diamine of the formula H and using 3.0 equivalents of chlorodiphenylphosphine (M. Tsukazaki, V. Snieckus et al., J. Am. Chem. Soc. 1996, 118, 685).

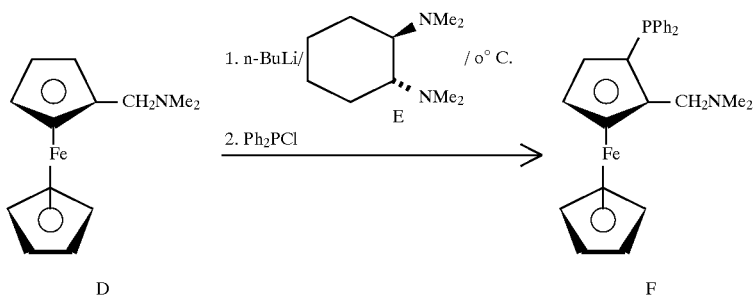

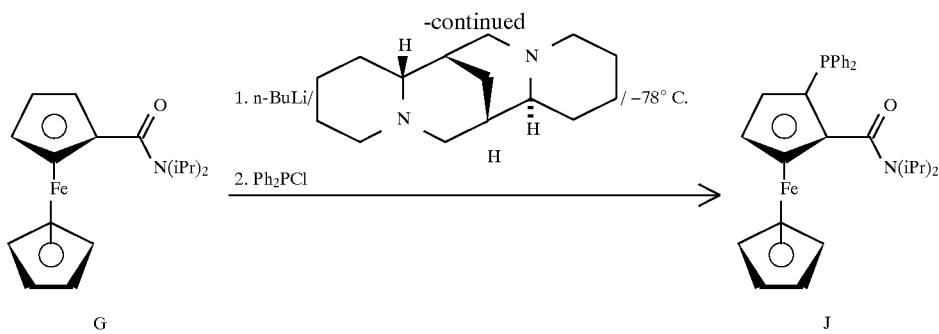

Whereas, therefore, an asymmetric ortho-lithiation on one ring of the ferrocene is known, there are no indications that it might be possible to extend this principle to both rings; no attempt has yet been made to apply the method of asymmetric ortho-lithiation using an optically active lithium base to both ferrocene rings.

Surprisingly, a very simple process has now been found for preparing phosphino-ferrocenes which is based on the principle of asymmetric ortho-lithiation. Such a lithiation is applied here for the first time to both ferrocene rings, and is used for the first time for the asymmetric synthesis of chiral $C_2$-symmetric diphosphino-ferrocenes. Starting, for example, from the commercially available 1,1'-ferrocenedicarboxylic acid it is thereby possible with great ease, by an extremely short synthetic route, to obtain novel monophosphino- and diphosphino-ferrocenes which are suitable as ligands for catalytically active transition metal complexes. By varying the novel process there are thus readily obtainable alternatively, inter alia, optically active 1',2-disubstituted 1-phosphino-ferrocenes of the formula Ib or optically active 2,2'-disubstituted 1,1'-diphosphino-ferrocenes of the formula Ia or, in a highly diastereoselective manner, the achiral meso isomers of the diphosphines Ia, i.e. the compounds of the formula II.

The present invention therefore provides, firstly, compounds of the formula I

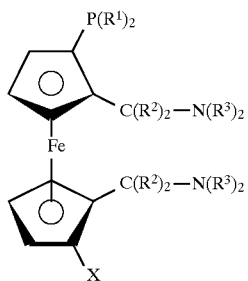

in which
the substituents $R^1$ are cyclohexyl, unsubstituted phenyl $C_6H_5$ or substituted phenyl $C_6H_{5-n}R^4{}_n$, where n is 1 to 5 and the substituents $R^4$ are unbranched or branched $C_1$- to $C_4$-alkyl, $C_1$- to $C_4$-alkoxy or halogen;
the two geminal substituents $R^2$ together are a doubly bonded oxygen atom (i.e. $(R^2)_2$ is =O) or each substituent $R^2$ on its own is hydrogen;
the substituents $R^3$, each on their own, are unbranched or branched $C_1$- to $C_4$-alkyl, cyclopentyl, cyclohexyl, unsubstituted phenyl $C_6H_5$ or substituted phenyl $C_6H_{5-n}R^4{}_n$, where n and $R^4$ are as defined above under $R^1$, or the substituents $R^3$ are connected to one another to form a ring, in which case together they are tetramethylene —$(CH_2)_4$—, pentamethylene —$(CH_2)_5$—, 3-oxapentamethylene —$(CH_2)_2$—O—$(CH_2)_2$— or N-methyl-3-azapentamethylene —$(CH_2)_2$—N($CH_3$)—$(CH_2)_2$—;
the substituent X is hydrogen or $P(R^1)_2$;
and salts thereof.

The conformations represented in the formula I and in other formulae, for example the formula II, do not necessarily correspond to the conformations in which the novel compounds are actually present under specific conditions and which are evident, for example, from the X-ray structural analyses. The formulae serve only to depict the arrangement of substituents on the ferrocene system and should not be understood as being restrictive in terms of a particular steric arrangement. Various conformations of the novel compounds are obtained, inter alia, especially by rotating one of the two ferrocene rings about an axis of rotation which passes through the center points of both rings. Which conformation with respect to this axis is actually present depends on the individual circumstances. The invention of course comprises all compounds of the formulae I and II (and their complexes) regardless of the particular configuration or conformation depicted graphically.

The present invention embraces, first, the free compounds of the formula I, i.e. the compounds which are not salts. However, the invention also embraces, second, the salts of compounds of the formula I. It is possible, for example, for compounds of the formula I, especially those which include basic groups, i.e. compounds, for example, in which the radicals $R^2$ are hydrogen, to form acid addition salts with inorganic and organic acids, especially with nonoxidizing acids. Examples of suitable acids are hydrochloric acid, hydrobromic acid, hydroiodic acid, sulfuric acid, nitric acid, phosphoric acid, acetic acid, trifluoroacetic acid, methanesulfonic acid, etc. The salts can be prepared in the customary manner, for example by combining the components in a solvent or diluent. Generally, the invention embraces the compounds of the formula II even when they are in the form of adducts with other molecules or ions or atoms, as is the case, for example, in complexes with metal ions or acid-base adducts.

The invention embraces all stereoisomeric forms of the compounds of the formula I, i.e. all enantiomeric and diastereomeric forms, and in particular it embraces both one enantiomer as well as the other enantiomer. The compounds of the formula I may have no further chirality elements besides the chirality resulting from the arrangement of the substituents on the ferrocene, however, it is also possible, for example, that additionally asymmetric carbon atoms are present in the radicals $R^1$ and $R^3$. These atoms may then, independently of one another, have the R or the S configuration. Enantiomers are embraced both in the form of pure enantiomers and in the form of the racemate or in the form of mixtures of the enantiomers in whatever proportions, especially in the form of mixtures having a high enantiomeric excess. Similarly, all diastereomers are embraced, in pure form and in mixtures with whatever proportions.

The invention similarly embraces mixtures of two or more compounds of the formula I which differ in the empirical formula, especially mixtures of compounds of the formula I in which X is hydrogen and the corresponding compounds of the formula I in which X is $P(R^1)_2$, in which case all compounds can, yet again, be present in all stereoisomeric forms.

Examples of $C_1$- to $C_4$-alkyl are methyl, ethyl, n-propyl, isopropyl, n-butyl, sec-butyl, isobutyl and tert-butyl; examples of $C_1$- to $C_4$-alkoxy are methoxy, ethoxy, n-propoxy, isopropoxy, n-butoxy, sec-butoxy, isobutoxy and tert-butoxy. In substituted phenyl radicals the substituents can be in any positions; in the case of monosubstitution, in the ortho, meta or para position; in the case of disubstitution, in the 3,4 or 3,5 position, for example. Where phenyl rings are substituted multiply by radicals $R^4$, then the radicals $R^4$ can be identical or different. The number n of the substituents in phenyl rings can be 1, 2, 3, 4 or 5. Among the substituted phenyl radicals, monosubstituted phenyl rings are preferred.

Unless specified otherwise, halogen is fluorine, chlorine, bromine or iodine.

The two radicals $R^1$ in the group $P(R^1)_2$ in the compounds of the formula I can be identical or different. In a preferred embodiment of the invention they are identical. The two radicals $R^3$ on the nitrogen atom can also, unless connected to one another to form a ring, be identical or different. Where the two radicals $R^3$ are connected to one another to form a ring, then this means that the two radicals $R^3$ which are attached to the same nitrogen atom are connected to one another and, thus, the radical $N(R^3)_2$ therefore is pyrrolidino, piperidino, morpholino or N-methylpiperazino.

$R^1$ in the compounds of the formula I is preferably cyclohexyl, phenyl, p-tolyl, p-tert-butylphenyl or p-halophenyl, in which case halogen here is fluorine, chlorine or bromine. With particular preference $R^1$ is phenyl.

The two radicals $R^2$ in the compounds of the formula I are preferably, together, a doubly bonded oxygen atom (i.e. $(R^2)_2$ is =O).

$R^3$ in the compounds of the formula I is preferably isopropyl, cyclohexyl or phenyl or the two radicals $R^3$ together are preferably —(CH$_2$)$_4$—, —(CH$_2$)$_5$—, —(CH$_2$)$_2$—O—(CH$_2$)$_2$— or —(CH$_2$)$_2$—N(CH$_3$)—(CH$_2$)$_2$—; with particular preference, $R^3$ is isopropyl.

X in the compounds of the formula I is preferably hydrogen or is a group $P(R^1)_2$ in which $R^1$ has the preferred definitions stated.

Preferred compounds of the formula I are those in which one or more of the substituents have preferred definitions. Particular preference is given to compounds of the formula I in which the substituents $R^1$ are cyclohexyl, phenyl, p-tolyl, p-tert-butylphenyl or p-halophenyl, in which case halogen here is fluorine, chlorine or bromine;

the two substituents $R^2$ together are a doubly bonded oxygen atom (i.e. $(R^2)_2$ is =O) or each substituent $R^2$ by itself is hydrogen;

the substituents $R^3$ are isopropyl, cyclohexyl or phenyl, or the two substituents $R^3$ together are —(CH$_2$)$_4$—, —(CH$_2$)$_5$—, —(CH$_2$)$_2$—O—(CH$_2$)$_2$— or —(CH$_2$)$_2$—N(CH$_3$)—(CH$_2$)$_2$—;

the substituent X is hydrogen or $P(R^1)_2$ in which $R^1$ is cyclohexyl, phenyl, p-tolyl, p-tert-butylphenyl or p-halophenyl and halogen in this case is fluorine, chlorine or bromine.

Very particular preference is given to compounds of the formula I in which $R^1$ is phenyl, the two substituents $R^2$ together are a doubly bonded oxygen atom (i.e. $(R^2)_2$ is =O), $R^3$ is isopropyl and X is hydrogen or P(phenyl)$_2$. Preference is given, furthermore, on the one hand to the compounds of the formula I in optically active form and on the other hand to the compounds of the formula I in racemic form.

The above comments correspondingly apply to the preferred compounds; here too, where relevant, all stereoisomeric forms and their mixtures in whatever ratios, and also the salts of the compounds, are embraced.

The present invention additionally provides compounds of the formula II

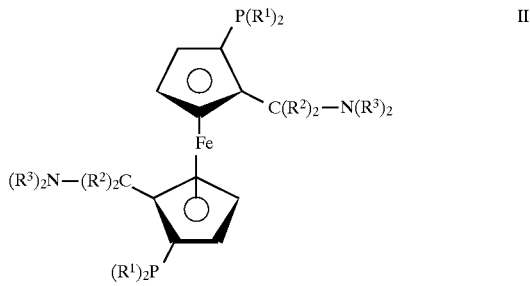

in which
the substituents $R^1$ are cyclohexyl, unsubstituted phenyl $C_6H_5$ or substituted phenyl $C_6H_{5-n}R^4_n$, where n is 1 to 5 and the substituents $R^4$ are unbranched or branched $C_1$- to $C_4$-alkyl, $C_1$- to $C_4$-alkoxy or halogen;

the two geminal substituents $R^2$ together are a doubly bonded oxygen atom (i.e. $(R^2)_2$ is =O) or each substituent $R^2$ on its own is hydrogen;

the substituents $R^3$, each on their own, are unbranched or branched $C_1$- to $C_4$-alkyl, cyclopentyl, cyclohexyl, unsubstituted phenyl $C_6H_5$ or substituted phenyl $C_6H_{5-n}R^4_n$, where n and $R^4$ are as defined above under $R^1$, or the substituents $R^3$ are connected to one another to form a ring, in which case together they are tetramethylene —(CH$_2$)$_4$— pentamethylene —(CH$_2$)$_5$—, 3-oxapentamethylene —(CH$_2$)$_2$—O—(CH$_2$)$_2$— or N-methyl-3-azapentamethylene —(CH$_2$)$_2$—N(CH$_3$)—(CH$_2$)$_2$—;

and salts thereof.

As in the case of the compounds of the formula I, the present invention embraces, first, the free compounds of the formula II, i.e. the compounds which are not salts. However, the invention also embraces, second, the salts of compounds of the formula II. It is possible, for example, for compounds of the formula II, especially those which include basic groups, i.e. compounds, for example, in which the radicals $R^2$ are hydrogen, to form acid addition salts with inorganic and organic acids, especially with nonoxidizing acids. Examples of suitable acids are hydrochloric acid, hydrobromic acid, hydroiodic acid, sulfuric acid, nitric acid, phosphoric acid, acetic acid, trifluoroacetic acid, methanesulfonic acid, etc. The salts can be prepared in the customary manner, for example by combining the components in a solvent or diluent. Generally, the invention embraces the compounds of the formula II even when they are in the form of adducts with other molecules or ions or atoms, as is the case, for example, in complexes with metal ions or acid-base adducts.

The achiral compounds of the formula II constitute the meso isomers of the chiral compounds of the formula Ia. The present invention also provides mixtures comprising compounds of the formula II and compounds of the formula I in whatever proportions. The comments regarding stereoisomeric forms and mixtures given above in relation to the compounds of the formula I apply here correspondingly; the compounds can, therefore, again be present in all stereoisomeric forms, and the mixtures may comprise two or more compounds, for instance compounds of the formulae Ia, Ib and II alongside one another.

The above comments regarding the radicals in the compounds of the formula I, for example alkyl radicals, alkoxy radicals, phenyl radicals or halogen, or the number n, apply likewise to the radicals in the compounds of the formula II. Again, the above comments regarding the preferred definitions of the radicals $R^1$, $R^2$ and $R^3$ and regarding the preferred compounds of the formula I apply correspondingly to the compounds of the formula II.

The present invention also provides processes for preparing compounds of the formulae I and II. In particular, the invention provides processes for preparing compounds of the formula Ia and Ib in optically active form, especially in high optical purity. These processes comprise, in the case of preparing compounds of the formula Ia, a twofold asymmetric ortho-lithiation and, in the case of preparing compounds of the formula Ib, a single asymmetric ortho-lithiation. By means of the novel processes it is possible, by varying the nature and amount of the lithium base, which may be chiral or achiral, and by modifying the precise lithiation procedure, to prepare—with very high chemoselectivity, diastereoselectivity and enantioselectivity—specifically, for example, the optically active $C_2$-symmetric diphosphines of the formula Ia or the achiral meso isomers of the diphosphines of the formula Ia, i.e. the compounds of the formula II, or the optically active asymmetric monophosphines of the formula Ib. The invention also embraces, however, the analogous preparation of the corresponding racemic compounds of the formula I.

As direct starting material for the novel preparation process it is possible to use compounds of the formula III,

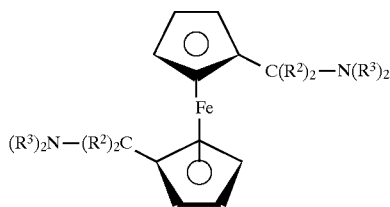

III in which the substituents $R^2$ and $R^3$ are as defined above. The compounds of the formula III can be obtained from commercially available 1,1'-ferrocenedicarboxylic acid. This can be reacted in one stage with high yields, in a manner known from the literature, to ferrocenediamides of the formula III in which the two geminal radicals $R^2$ together are a doubly bonded oxygen atom. In doing so the amide radicals $R^3$ can, in a manner known from the literature, be varied within the overall abovementioned range of definitions of $R^3$, which requires only the variation of the readily commercially available amine $HN(R^3)_2$ (P. J. Hammond et al., J. Organomet. Chem. 1986, 306, 367; P. D. Beer et al., J. Organomet. Chem. 1988, 350, C15; J. C. Medina et al., J. Am. Chem. Soc. 1991, 113, 365; J. T. Yli-Kauhaluoma et al., J. Am. Chem. Soc. 1995, 117, 7041; W. Zhang et al., Tetrahedron: Asymmetry 1996, 7, 451). The diamides of the formula III, i.e. the compounds of the formula III in which the two radicals $R^2$ together are a doubly bonded oxygen atom, can be reduced in accordance with methods known from the literature using various reducing agents, preferably with the borane-tetrahydrofuran complex, in high yields to the corresponding diamines of the formula III in which each radical $R^2$ on its own is hydrogen.

It has now been found that the reaction of compounds of the formula III in which the substituents $R^2$ and $R^3$ are as defined above with n-butyllithium in the presence of tertiary amines, preferably chelating tertiary diamines, takes place with almost complete mono-ortho-lithiation even when large excesses of the lithium base are used (>4 equivalents relative to the substrate III). If a chlorophosphine of the formula $ClP(R^1)_2$ in which the radicals $R^1$ are as defined above is then added to the reaction mixture, such chlorophosphines being obtainable by or in analogy to known methods and also, in the majority of cases, being commercially available, then the compounds of the formula Ib are obtained in high yields. If the lithium base is obtained by reacting n-butyllithium with an optically pure (homochiral) tertiary amine, preferably an optically pure chelating tertiary diamine, then the compounds of the formula Ib are formed with high enantioselectivity (in this application the term "homochiral" has the meaning "optically pure" or "enantiomerically pure" or the like). As evident from the Examples, this enantioselectivity is under appropriate reaction conditions so high (>80% ee (ee=enantiomeric excess)) that the compounds of the formula Ib can be obtained in good yields in optically pure form ($\geq$98% ee) directly or, for example, after only one recrystallization. If the lithium base is obtained by reacting n-butyllithium with a racemic or with an achiral tertiary amine, then under otherwise identical reaction conditions the compounds of the formula Ib are formed in racemic form.

The present invention accordingly provides a process for preparing optically active monophosphines of the formula I in which the radicals $R^1$, $R^2$ and $R^3$ are as defined above and X is hydrogen, which comprises subjecting compounds of the formula III

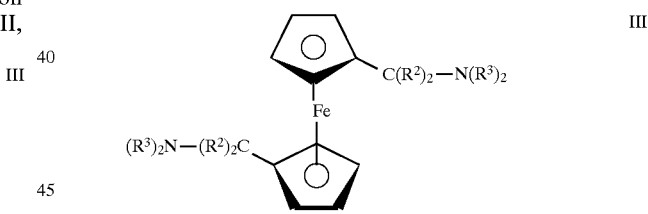

III in which the radicals $R^2$ and $R^3$ are as defined above to asymmetric mono-ortho-lithiation using n-butyllithium in the presence of a homochiral tertiary amine and reacting the chiral monolithium compound in-situ with a chlorophosphine of the formula $ClP(R^1)_2$ in which the radicals $R^1$ are as defined above.

If desired, the optical purity of the product of the formula I is subsequently increased further by recrystallization. The optical purity of the product of the formula I initially obtained by the novel process depends on the individual circumstances, for example on the substituents and on the reaction conditions. In many cases it is already high enough that no increase is necessary for the intended use. If it is desired to increase the optical purity, however, this can be done, for example, by recrystallization under conditions familiar to the skilled worker, in which case just one recrystallization is sufficient in many cases.

Specifically, the asymmetric reaction can be conducted, for example, as follows. The optically pure tertiary amine, preferably an optically pure chelatable tertiary diamine, is introduced as initial charge in an inert, noncoordinating or weakly coordinating solvent under an inert gas atmosphere (preferably nitrogen or argon), preferably at a temperature from −78° C. to room temperature, particularly preferably from −78° C. to 0° C. and, with very particular preference, at a temperature from −78° C. to −40° C. Particularly preferred amines are diamines such as, for example, sparteine, trans-N,N,N',N'-tetramethyl-1,2-cyclohexanediamine, N,N,N',N'-tetramethyl-1,2-diphenylethylenediamine, 1-methyl-2-(piperidinomethyl) pyrrolidine, O-alkyl-dihydroquinidines or O-alkyl-dihydroquinchonidines. Sparteine is very particularly preferred. The amines can be employed as (+)-isomer or as (−)-isomer. The amine is preferably employed in an amount of from 1.2 to 5 equivalents, based on the starting material of the formula III, particularly preferably in an amount of from 1.5 to 4 equivalents, and, with very particular preference, from 1.5 to 2 equivalents. Preferred solvents are aliphatic and aromatic hydrocarbons and ethers, particular preference being given to toluene, diethyl ether, methyl tert-butyl ether and diisopropyl ether. To the amine there is then added a solution of n-butyllithium in an inert solvent, preferably a 1 to 10 molar solution in pentane, hexane or cyclohexane, particularly preferably a 1.6 to 2.5 molar solution in hexane. The amount of n-butyllithium is preferably from 1.2 to 5 equivalents, based on the starting material of the formula III, particularly preferably from 1.5 to 4 equivalents and, with very particular preference, from 1.5 to 2 equivalents. It is preferred for the molar amount of n-butyllithium to be equal to or slightly less than that of the chiral amine, so that all of the n-butyllithium is in association with the chiral amine. Following a brief period of stirring, the starting material of the formula III is added, either as pure substance or, for example, dissolved in one of the abovementioned solvents. The rate of addition is not critical. The reaction temperature is maintained by cooling. Following a period of normally from 15 minutes to 2 hours (the optimum time period is shorter the greater the excess of n-butyllithium and of chiral amine), the chlorophosphine of the formula $ClP(R^1)_2$ is added as pure substance or, for example, as a solution in one of the abovementioned solvents. The rate of addition is largely uncritical. It is preferred to add liquid chlorophosphines dropwise, as pure substance, over the course of from 5 to 15 minutes, so that it is easy to maintain the reaction temperature by cooling. Stirring is continued generally for 15 to 90 minutes. The optimum reaction time depends on the solvent and on the substituents $R^1$, $R^2$ and $R^3$ and can easily be determined by removing a sample and by, for example, thin-layer chromatographic analysis on the basis of the disappearance of the compound of the formula III and the formation of the compound of the formula Ib. To isolate the product, the reaction mixture is preferably subjected to an aqueous workup under acidic conditions. For instance, after complete reaction the reaction mixture can be worked up, for example, by first heating it to a temperature from 0° to 25° C. or to room temperature and then adding to it, for example, an excess of a saturated aqueous solution of ammonium chloride ($NH_4Cl$). However, it is also possible, for example, to add an ammonium chloride solution at a lower temperature and only then to carry out heating. The results of these two procedures differ only slightly. The aqueous standard workup, for example with extraction, finally yields the optically active monophosphine of the formula Ib. The resulting products are of virtually no sensitivity to air as isolated solids but are moderately so in solution (formation of phosphine oxides). The extractions are therefore preferably undertaken in an inert gas atmosphere or with minimization of the time during which air can act.

As can be seen from the Examples, this procedure results—for example for the starting material of the formula III in which the radicals $R^2$ together are a doubly bonded oxygen atom and $R^3$ is isopropyl, even with 4.40 equivalents of n-butyllithium and 4.45 equivalents of (−)-sparteine in ether at a temperature from −70° to −78° C. with a lithiation time of 1 hour and using chlorodiphenylphosphine—in more than 85% of the monophosphine of the formula Ib and less than 15% of the diphosphines of the formulae II and/or Ia. In this case the crude product had 80% ee and can be purified further by standard purification techniques. In the example under consideration, for example, recrystallization from hot n-heptane gives the analytically pure compound of the formula Ib in a yield of 58% and with 98.5% ee. The optical purity can be determined reliably by means of HPLC on a chiral phase. With a reduced excess of n-butyllithium/sparteine and a reduced lithiation time, the proportion of the monophosphine of the formula Ib in the crude product is increased further. As can also be seen from the Examples, the same starting material of the formula III (with the same definitions of the radicals $R^2$ and $R^3$) results—with 1.9 equivalents of n-butyllithium and 2.0 equivalents of (−)-sparteine in toluene at −70° to −78° C., with a lithiation time of 45 minutes and using chlorodiphenylphosphine—in more than 93% of the monophosphine of the formula Ib, which even as crude product has 91% ee. Single recrystallization then gives the optically pure (99% ee) product of the formula Ib in a yield of 75%.

If the above reaction is carried out in ether as solvent with the achiral diamine N,N,N',N'-tetramethylethylenediamine (TMEDA) instead of with an optically active amine such as sparteine, under otherwise identical conditions as described by way of example above, then the racemic compound of the formula Ib is obtained in a yield of 79%.

If the asymmetric lithiation/phosphinylation of substrates of the formula III is carried out under conditions identical to those described above but using sec-butyllithium instead of n-butyllithium, then the corresponding meso-diphosphines of the formula II are obtained with high chemoselectivity and diastereoselectivity. Chiral $C_2$-symmetric diphosphines of the formula Ia and monophosphines of the formula Ib are formed in very small quantities under these conditions even if the excess of the lithium base is reduced to 3.0 equivalents. The high diastereoselectivity in favor of the compounds of the formula II relative to those of the formula Ia is a complete surprise. Although the two ortho-lithiations on the upper and the lower ring of the ferrocene must indeed be brought about by the same homochiral lithium base, with sec-butyllithium the ortho-lithiation/phosphinylation takes place on the lower ferrocene ring with an enantioselectivity just opposite to that on the upper ferrocene ring.

The present invention accordingly provides, furthermore, a process for preparing compounds of the formula II in which the radicals $R^1$, $R^2$ and $R^3$ are as defined above, which comprises subjecting compounds of the formula III

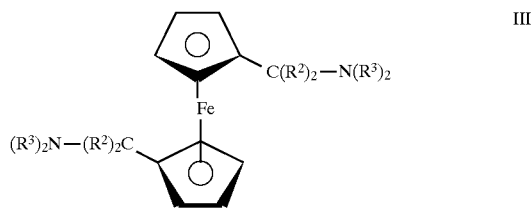

in which the radicals $R^2$ and $R^3$ are as defined above to ortho-lithiation with sec-butyllithium in the presence of a tertiary amine, preferably in the presence of a chelatable tertiary diamine, particularly preferably in the presence of an achiral or racemic chelatable tertiary diamine, for example in the presence of N,N,N',N'-tetramethylethylenediamine (TMEDA), and reacting the dilithium compound in-situ with a chlorophosphine of the formula $ClP(R^1)_2$ in which the radicals $R^1$ are as defined above.

The comments made above regarding the process for preparing compounds of the formula Ib, relating, for example, to the amines, the solvents, the amounts or the reaction temperatures, apply here correspondingly. When, however,—as here—the aim is to achieve twofold lithiation/phosphinylation of the ferrocene in a preparation process, the minimum amount of lithiating reagent employed is of course greater and is at least 2 equivalents, based on the starting material of the formula III. The majority of diphosphines of the formula II are virtually insoluble in water and are sparingly to very moderately soluble in the abovementioned reaction solvents. If the reaction mixture is, as described by way of example above, worked up by addition of aqueous ammonium chloride solution, then the compounds of the formula II precipitate out and can in many cases be isolated by simple suction filtration.

As can be seen from the Examples, this results—for example for the starting material of the formula III in which the radicals $R^2$ together are a doubly bonded oxygen atom and $R^3$ is isopropyl, using sec-butyllithium and (−)-sparteine in ether at from −70° to −78° C., with a lithiation time of 2 hours and using chlorodiphenylphosphine—in a crude product with a ratio of compound II: compound Ia of about 95:5. This ratio has been determined unanimously by various methods. The pure meso-diphosphine is obtained in 75% yield after recrystallization. Apart from by means of spectra, the structure of the compound of the formula II is ascertained by a single-crystal X-ray structural analysis. If the achiral diamine TMEDA is employed instead of sparteine, then the meso-diphosphine of the formula II is obtained in 64% yield with the same high diastereoselectivity.

If, in contrast, the asymmetric dilithiation/diphosphinylation of the starting materials of the formula III is carried out not in one go but stepwise, by subjecting the optically active monophosphines of the formula Ib obtained as described above once again to the same conditions under which they were formed, then the optically pure chiral, $C_2$-symmetric diphosphines of the formula Ia are obtained with very high diastereoselectivity with virtually quantitative conversion of the monophosphines of the formula Ib. The two stepwise monolithiations/monophosphinylations, induced by a chiral lithium base formed from n-butyllithium and a homochiral tertiary amine, take place accordingly with the same enantioselectivity on the lower and on the upper ferrocene ring.

The present invention therefore also provides a process for preparing optically active $C_2$-symmetric diphosphines of the formula I, in which the radicals $R^1$, $R^2$ and $R^3$ are as defined above and X is $P(R^1)_2$, which comprises subjecting the optically active monophosphines of the formula I in which the radicals $R^1$, $R^2$ and $R^3$ are as defined above and X is hydrogen, to asymmetric mono-ortho-lithiation with n-butyllithium in the presence of a homochiral tertiary amine, and reacting the chiral monolithium compound in-situ with a chlorophosphine of the formula $ClP(R^1)_2$ in which the radicals $R^1$ are as defined above.

If desired, here too the optical purity of the product of the formula I is subsequently raised further by recrystallization. The optical purity of the product of the formula I initially obtained by the novel process again depends on the individual circumstances, for example on the substituents and the reaction conditions. Here again, the optical purity of the product obtained directly by the novel process is in many cases already so high that no further increase is necessary for the intended use. If it is desired to increase the optical purity, this can be done by recrystallization under conditions familiar to the skilled worker, in which case just one recrystallization is sufficient in many cases.

The comments made above regarding the process for preparing compounds of the formula Ib, in relation, for example, to the amines, the solvents, the amounts or the reaction temperatures, apply here correspondingly. Similarly to the meso-diphosphines of the formula II, the majority of $C_2$-symmetric diphosphines of the formula Ia are also virtually insoluble in water and of only moderate solubility in the abovementioned reaction solvents. If working up is carried out as described above by way of example, then they can therefore be isolated not only by conventional extraction, preferably with methylene chloride, but frequently also by simple suction filtration, in which case, however, a reduction in yield ranging from small to marked must be taken into account. In the examples investigated to date the crude diphosphines of the formula Ia in solution were more sensitive to air than the meso-diphosphines of the formula II, although the purified compounds of the formula Ia showed virtually no sensitivity to air as solids and only moderate air-sensitivity in solution.

As can be seen from the Examples, this results—for example starting from the starting material of the formula Ib in which $R^1$ is phenyl, the two radicals $R^2$ together are a doubly bonded oxygen atom, $R^3$ is isopropyl and X is hydrogen and which has 98.5% ee, with 2.1 equivalents of n-butyllithium and 2.2 equivalents of (−)-sparteine in ether at −70° to −78° C., with a lithiation time of 30 minutes and using chlorodiphenylphosphine, with virtually quantitative conversion of the starting material of the formula Ib—in a crude product comprising the $C_2$-symmetric diphosphine of the formula Ia and the meso-diphosphine of the formula II in a ratio of 97:3. This ratio has been determined unanimously by various methods. The crude product contains >90% of theory of compound of the formula Ia. If a racemic rather than an optically pure monophosphine of the formula Ib is employed as starting material for the second lithiation/phosphinylation step, then, using a homochiral amine, the optically active $C_2$-symmetric diphosphine of the formula Ia is obtained in a mixture with the corresponding meso-diphosphine of the formula II. If the starting material in the second lithiation step is racemic monophosphine of the formula Ib, and an achiral amine is used, then racemic diphosphine of the formula Ia is obtained.

To prepare optically active $C_2$-symmetric compounds of the formula I in which X is $P(R^1)_2$, it is also possible to carry out both ortho-lithiation/phosphinylation steps without isolating the initially formed monophosphine, for example in a one-pot process. This process, which is also provided by the present invention, comprises first of all deprotonating a compound of the formula III

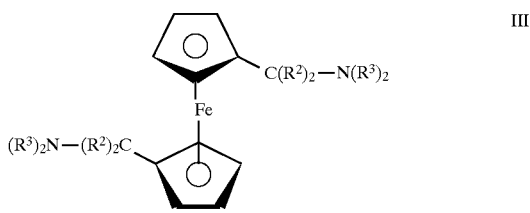

in which $R^2$ and $R^3$ are as defined above with n-butyllithium in the presence of a homochiral tertiary amine, for example sparteine, then phosphinylating the product by adding a chlorophosphine of the formula $ClP(R^1)_2$ in which $R^1$ is as defined above, and which is preferably employed in as small an excess as possible, then, without isolating the resulting monophosphine, performing the second deprotonation step by again adding n-butyllithium, and, finally, effecting the second phosphinylation by again adding the chlorophosphine of the formula $ClP(R^1)_2$. This process too is subject correspondingly to the comments made above regarding the preparation of the compounds of the formulae Ib and II, in relation, for example, to the amines, the solvents, the amounts, the reaction temperatures or, if appropriate, to recrystallizations to be carried out in order to increase the purity.

Finally, the present invention provides a process for preparing racemic compounds of the formula I in which the radicals $R^1$, $R^2$, $R^3$ and X are as defined above, i.e. in which X is hydrogen in the case of racemic monophosphines and is $P(R^1)_2$ in the case of racemic $C_2$-symmetric diphosphines, which comprises subjecting achiral ferrocenes of the formula III

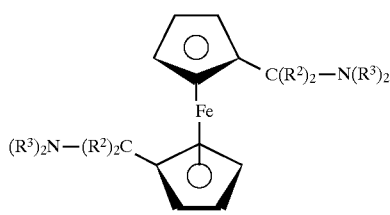

III in which the radicals $R^2$ and $R^3$ are as defined above, or racemic monophosphines of the formula I in which X is hydrogen, to symmetric mono-ortho-lithiation using n-butyllithium in the presence of a racemic or achiral tertiary amine, for example in the presence of N,N,N',N'-tetramethylethylenediamine (TMEDA), and reacting the monolithium compound in-situ with a chlorophosphine of the formula $ClP(R^1)_2$ in which the radicals $R^1$ are as defined above, or, in the case of the preparation of the diphosphines from the compounds of the formula III, carrying out stepwise symmetric dilithiation/diphosphinylation. To this process, too, the above comments apply correspondingly.

The monophosphines and diphosphines of the formulae I and II in which the radicals $R^2$ are hydrogen can be prepared not only by asymmetric ortho-lithiation of, for example, the N,N-disubstituted 1,1'-bis(aminomethyl)ferrocenes of the formula III in which the radicals $R^2$ are hydrogen but also by reduction of the corresponding bisamides of the formulae I and II in which the two radicals $R^2$ together are a doubly bonded oxygen atom. The reduction can be carried out in accordance with known techniques using various reducing agents. It is preferably carried out with the borane-tetrahydrofuran complex. In this case, the initial products are the borane adducts of the compounds of the formulae I and II in which the radicals $R^2$ are hydrogen, from which it is then possible to prepare the free phosphines or the transition metal catalysts in a manner known per se (cf. A. R. Muci, K. R. Campos, D. A. Evans, J. Am. Chem. Soc. 1995, 117, 9075).

The novel compounds of the formulae I and II are suitable as ligands for catalytically active transition metal complexes. The present invention therefore also embraces the use of compounds of the formulae I and II as ligands in connection with the preparation of transition metal complexes, and the use of the compounds as ligands in such complexes. Preferred transition metal elements are the elements ruthenium, rhodium, iridium, nickel, palladium, platinum, silver, copper and gold, particular preference being given to the elements ruthenium, rhodium, iridium, nickel, palladium, platinum and silver. The invention embraces in particular the use of chiral and/or optically active compounds of the formula I as ligands in chiral transition metal complexes. In accordance with customary procedures described in the literature, which to that extent are included fully herein by reference, the novel compounds, especially the optically active phosphines of the formula I, can be reacted in analogy to the Hayashi ligands of the formulae A, B and C to form isolated complexes or in-situ complexes of the transition metals, particularly preferably to form complexes of ruthenium, rhodium, iridium, nickel, palladium, platinum or silver (see T. Hayashi et al., Tetrahedron Lett. 1980, 21, 1871 and J. Am. Chem. Soc. 1982, 104, 180; W. R. Cullen et al., Organometallics 1985, 4, 346; Ferrocenes, A. Togni and T. Hayashi (Edit.), VCH, Weinheim, 1995; H.-U. Blaser, F. Spindler, ChimiaOggi 1995, June, page 11; N. C. Zanetti, F. Spindler, J. Spencer, A. Togni, G. Rihs, Organometallics 1996, 15, 860). Preference is given to the use of optically pure or substantially optically pure compounds of the formula I for the preparation of optically pure or substantially pure transition metal complexes and to the use of such compounds as ligands in such complexes. The invention, however, similarly embraces the corresponding use of racemic compounds of the formula I and achiral compounds of the formula II in connection with the preparation of racemic or achiral transition metal complexes, and the use as ligands in such complexes, again preferably complexes of ruthenium, rhodium, iridium, nickel, palladium, platinum, silver, copper or gold, particular preference being given to complexes of ruthenium, rhodium, iridium, nickel, palladium, platinum or silver.

Finally, the invention also provides the complexes of compounds of the formulae I and II in which the substituents $R^1$, $R^2$, $R^3$ and X have the general or preferred definitions given above with transition metals, preferably with the transition metals ruthenium, rhodium, iridium, nickel, palladium, platinum, silver, copper and gold, particularly preferably with the transition metals ruthenium, rhodium, iridium, nickel, palladium, platinum and silver, and for the use of such complexes as catalysts in catalytic reactions. The novel complexes comprise at least one ligand of the formulae I or II (in other words, they comprise one ligand which is a compound of the formulae I or II or they comprise more than one ligands which are compounds of the formulae I or II). As further ligands they may comprise one or more inorganic and/or organic ions and/or molecules. The choice of further ligands which can be present in the complexes depends, for example, on the intended use. The transition metals can be present in the complexes in their customary valences. The novel transition metal complexes, both in isolated form and produced in-situ, are useful catalysts for numerous reactions of organic compounds. Preference is given to the transition metal complexes with optically pure ligands of the formula I, which can be used as useful catalysts in asymmetric catalytic reactions. Examples of some such reactions are set out in the following overview:

hydrogenations of prochiral C=O, C=C and C=N groups;

coupling reactions of the Heck type with or without carbon monoxide insertion;

cross-couplings of organometallic compounds (e.g. Grignard compounds) with organic halides;

hydrosilylations, hydroborations and hydroformylations of prochiral C=O, C=C and C=N groups;

nucleophilic substitutions on substrates having a nucleofugic leaving group in the allylic position;

isomerizations of allylamines to the corresponding enamines.

Compilations of recent literature regarding such asymmetric reactions can be found in I. Ojima, Catalytic Asymmetric Synthesis, VCH, Weinheim, 1993 and in R. Noyori, Asymmetric Catalysis in Organic Synthesis, Wiley Interscience, 1994.

The invention, however, just so embraces the corresponding racemic transition metal complexes and achiral transition metal complexes, preferably of the elements ruthenium, rhodium, iridium, nickel, palladium, platinum, silver, copper and gold, particularly preferably of the elements ruthenium, rhodium, iridium, nickel, palladium, platinum and silver, which comprise racemic or achiral compounds of the formulae I or II as ligands, and the use of these complexes as racemic catalysts, especially for the symmetric variants of the catalytic reactions set out in the above overview.

EXAMPLES

General notes: Diethyl ether was distilled off freshly in a nitrogen atmosphere from sodium/benzophenone ketyl. (−)-Sparteine was distilled off freshly under vacuum through a short Vigreux column from calcium hydride. Chlorodiphenylphosphine was distilled freshly under a high vacuum (HV) through a short Vigreux column. Before introducing reagents, all solvents used were freed from dissolved oxygen by bubbling argon through them. In the course of workups, air contact was minimized by passing argon through all solvents and working rapidly. As crystalline solids, all of the ferrocene compounds described here have virtually no sensitivity to air. In solution they are all more or less sensitive, especially the crude $C_2$-symmetric diphosphines of the formula Ia. NMR-spectroscopic shifts are given in ppm. Me denotes methyl, Et ethyl, iPr isopropyl, Ph phenyl, Bu butyl and BuLi butyllithium. Preparation of the starting compound 1,1'-bis(N,N-diisopropylamido)-ferrocene (formula II, $(R^2)_2$:=O, $R^3$:iPr); synthesis method 1

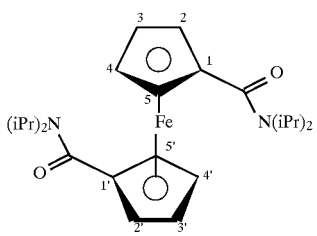

12.0 g (43.8 mmol) of 1,1'-ferrocenedicarboxylic acid (Aldrich) were suspended in 63 ml of toluene which had been degassed beforehand by means of a stream of argon bubbling through it. Under an argon atmosphere, 15.2 ml (22.2 g, 174.9 mmol) of oxalyl chloride were added over the course of 5 minutes using a syringe, followed by 1.2 ml of dimethylformamide. A vigorous reaction ensued, accompanied by foaming and gas evolution, but without any notable discernible exothermy. The mixture was stirred at room temperature for 10 minutes. The excess oxalyl chloride was removed in vacuo on a rotary evaporator (bath temperature 30° C.) by concentrating the reaction mixture to a total volume of from 20 to 30 ml. The suspension, which was still readily stirrable, was diluted with 250 ml of diethyl ether and then cooled to 0° C. under argon. 32.2 ml (24.9 g, 245.9 mmol) of diisopropylamine were added dropwise over the course of 10 minutes. Because of the exothermic reaction, the internal temperature rose temporarily to +5° C. The color of the suspension changed from dark orange to pale yellow. After stirring at 0° C. for 1 hour a 0.5 ml sample was removed, 0.5 ml of saturated aqueous ammonium chloride solution and 0.5 ml of diethyl ether were added to it, and it was analyzed by thin-layer chromatography (TLC) using the eluent cyclohexane/ethyl acetate (1:1), where complete reaction of the dicarboxylic acid ($R_f$=0.00) to the title compound ($R_f$=0.37) and small amounts of a somewhat more polar byproduct ($R_f$=0.25) was found. After further stirring for one hour, 200 ml of saturated ammonium chloride solution and 50 ml of water (both argon-degassed) were added with ice cooling. The mixture was subjected to extraction with twice 200 ml of dichloromethane, during which argon was bubbled through. At the phase boundary there was deposited a black stuff which was separated off with the aqueous phase. The combined extracts were washed with twice 250 ml of water and then with 250 ml of saturated sodium chloride solution. The organic phase was dried over $MgSO_4$ for 5 minutes and filtered, the filtrate was concentrated in vacuo, and the solid was dried in vacuo. 17.2 g (39.0 mmol, 89% yield) were obtained of an orange-yellow solid which according to TLC contained a slight amount of more polar impurities. Filtration through silica gel with cyclohexane/ethyl acetate (3:1) gave 15.0 g (34.1 mmol, 78% yield) of a yellow, very bulky solid, m.p. 136°–137° C. (Lit.: P. J. Hammond et al., J. Organomet. Chem. 1986, 306, 367; m.p. 127°–128° C.).

$^1$H-NMR (200 MHz, $CDCl_3$): d=4.59 (t, J=2 Hz, 4H, 2-,2'-,5-,5'-H), 4.43 (br s, 2H, $CHMe_2$), 4.38 (t, J=2 Hz, 4H, 3-,3'-,4-,4'-H), 3.43 (br s, 2H, $CHMe_2$), 1.47 (br s,12H, $CH(CH_3)_2$), 1.20 (brs, 12 H, $CH(CH_3)_2$).

$^{13}$C-NMR (75.43 MHz, $CDCl_3$, proton broadband-decoupled; multiplicity determined using DEPT 135°): d=168.80 (2C, C=O), 83.23 (2C, 4°-C, C-1,-1'), 71.36 (4C, CH, C-2,-2',-5,-5'), 70.95 (4C, CH, C-3,-3',-4,-4'), 49.85 (2C, br, CH, $CHMe_2$), 46.19 (2C, br, CH, $CHMe_2$), 21.09 (8C, $CH_3$).

IR (KBr): n=2968, 1633 (C=O), 1619 (C=C of aryl), 1465, 1317 $cm^{-1}$. MS (FAB, NBA): m/z (%)=441 (55) [M+H$^+$], 440 (100) [M$^+$], 340 (22) [M+H$^+$-HN(iPr)$_2$], 248 (15) [$C_{12}H_{18}FeNO^+$].

Preparation of the starting compound 1,1'-bis(N,N-diisopropylamido)-ferrocene (formula III, $(R^2)_2$:=O, $R^3$:iPr); synthesis method 2

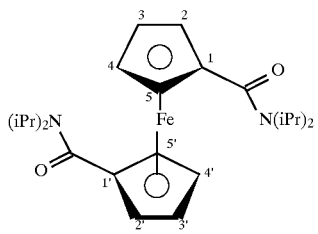

To a solution of 10.0 g (36.5 mmol) of 1,1'-ferrocenedicarboxylic acid in 200 ml of degassed toluene there were added at room temperature and under argon 10.0 ml (14.55 g, 114.6 mmol) of oxalyl chloride followed immediately by 1.0 ml (944 mg, 12.9 mmol) of dimethylformamide. The reaction ensued with foaming and vigorous gas evolution but without notable exothermy. Without cooling, the internal temperature rose to a maximum of 24° C. The mixture was stirred at room temperature for 10 minutes and then the excess oxalyl chloride was removed by concentrating the mixture to a quarter of its original volume in vacuo. The concentrated solution was diluted with 250 ml of toluene and cooled in an ice bath to 0° C., while bubbling argon through it. Then 11.2 ml (8.13 g, 80.3 mmol) of degassed triethylamine and 9.6 ml (7.41 g, 73.2 mmol) of degassed diisopropylamine were added dropwise in succession. The dark red-brown, clear solution was stirred at 0° C. for 1 hour and then at room temperature for 16 hours. A further 4.8 ml (3.70 g, 36.6 mmol) of degassed diisopropylamine were added dropwise and the mixture was stirred at room temperature for 18 hours more. Working up as described for synthesis method 1 gave 14.3 g (32.5 mmol, crude yield 89% of theory) of orange-brown solid which contained the same more polar byproduct as the product obtained by synthesis method 1. Filtration through 300 g of silica gel with cyclohexane/ethyl acetate (3:1) gave 9.9 g (22.5 mmol, 62% yield) of the title compound as a yellow solid, m.p.134°–135° C., decomposition at 258°–262° C. with black coloration and clouding of the melt.

Example 1

1-(Diphenylphosphino)-1',2-bis(N,N-diisopropylamido) ferrocene (formula Ib, $R^1$:Ph, $(R^2)_2$=O, $R^3$:iPr); preparation using 4.40 equivalents of n-BuLi and 4.45 equivalents of (−)-sparteine in diethyl ether

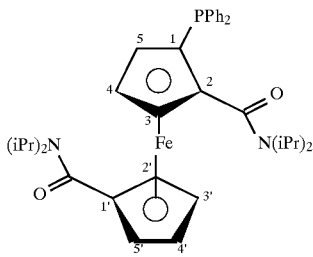

19.25 ml (30.8 mmol) of a 1.6 molar solution of n-butyllithium in hexane were added dropwise over the course of 5 minutes at −78° C., under argon, to a solution of 7.30 g (7.16 ml, 31.15 mmol) of (−)-sparteine in 130 ml of diethyl ether. The initially clear, yellowish solution turned into a white suspension after about 5 minutes. Stirring was continued at −78° C. for 15 minutes and then a solution of 3.08 g (7.0 mmol) of 1,1'-bis(N,N-diisopropylamido) ferrocene in 35 ml of diethyl ether was added dropwise over the course of 10 minutes. The deep yellow suspension was stirred at −78° C. under argon for 1 hour, and then 7.5 ml (9.27 g, 42.0 mmol) of chlorodiphenylphosphine were added dropwise over the course of 5 minutes using a syringe. Over the course of a further 5 minutes the yellow suspension turned into a clear, brown solution which was stirred at −78° C. for 30 minutes. A sample (0.5 ml) was taken, to which saturated ammonium chloride solution (0.5 ml) and $Et_2O$ (0.5 ml) were added, and the resulting sample was investigated by TLC using the eluent cyclohexane/ethyl acetate (3:1). It was found that the starting material of the formula III ($R_f$=0.20) had reacted completely to form a product (title compound; Rf=0.34). The corresponding diphosphines of the formulae II and/or Ia ($R_f$=0.52, not separated from one another) were detectable only in traces. 30 minutes after the sample had been taken (1 hour after the chlorophosphine had been added) the mixture was heated to +20° C. and then 160 ml of saturated aqueous ammonium chloride were added dropwise over the course of 5 minutes. The mixture was stirred for 15 minutes and then the phases were separated. The aqueous phase was extracted with 2×100 ml of ether, the combined ether phases were washed with 200 ml of water, then with 200 ml of saturated sodium chloride solution, dried over $MgSO_4$ and filtered, and the filtrate was concentrated in vacuo. A $^{31}$P-NMR spectrum of the crude product ($CDCl_3$) showed the resonance of the title compound of the formula Ib (d=−22.92) and the resonance of the corresponding $C_2$-symmetric diphosphine of the formula Ia (d=−22.00) in a ratio of 95:5. The corresponding meso-diphosphine of the formula II (d=−22.38) could not be seen (<0.5%). The residue (10.4 g) was purified by flash chromatography (200 g of silica gel 60 Å, 35–70 mm, eluent cyclohexane/ethyl acetate (3:1), 1.25 bar of nitrogen) and gave 3.95 g (6.32 mmol, 90% of theory) of a yellow solid which had 80.0% ee according to chiral phase HPLC analysis (250×4.6 mm CSP Chiralpak AD; eluent: n-hexane/EtOH (20:1) plus 0.1% of diethylamine, flowrate 1.0 ml/min., 40° C., det. 248 nm; $t_{ret}$ (%): (+)-title compound of the formula Ib 6.21 min (90.0%), (−)-title compound of the formula Ib 4.60 min. (10.0%)). Recrystallization from 30 ml of hot, argon-degassed n-heptane gave 2.52 g (4.03 mmol, 58% of theory) of yellow crystals, m.p. 146°–148° C. (decomp.), $[a]_D^{20}$=+235.8° (c=1.013 in $CH_2Cl_2$), which according to chiral phase HPLC analysis had 98.5% ee of the (+)-enantiomers of the title compound.

$^1$H-NMR (300 MHz, $CDCl_3$): d=7.53 (m, 2H, p-H of $C_6H_5$), 7.16–7.40 (m, 8H, o- and m-H of $C_6H_5$), 4.80 (dt, $J_d$=2.5 Hz, $J_t$=1.3 Hz, 1 H, 2'-H), 4.65 (td, $J_t$=2.5 Hz, $J_d$=1.4 Hz, 1 H, 3'-H), 4.52 (dt, $J_d$=2.5 Hz, $J_t$=1.3 Hz, 1 H, 5'-H), 4.45 (t, J=2.5 Hz, 1 H, 4-H), 4.38 (br s, 1 H, $CHMe_2$), 4.36 (dt, $J_d$=2.5 Hz, $J_t$=1.2 Hz, 1 H, 3-H), 4.25 (td, $J_t$=2.5 Hz, $J_d$=1.2 Hz, 1H, 4'-H), 3.91 (m, 1 H, 5-H), 3.87 (br s, 1 H, $CHMe_2$), 3.38 (br s, 1 H, $CHMe_2$), 3.18 (br s, 1 H, $CHMe_2$), 0.90–1.57 (m, 21 H, 7×$CH_3$), 0.50 (m, 3H, $CH_3$).

The assignment of the $^1$H resonances to the seven protons of the two ferrocene rings is based on the assumption that the compound is predominantly present in the conformation set out in the formula in Example 1, on considerations regarding the relative influencing of the protons in this molecule conformation by anisotropies of the two carbonyl groups and the phenyl rings, and on an interpretation of the size of the coupling constants. It cannot be completely ruled out that the assignments of the following proton pairs should be swapped: 2'-H with 5'-H; 3'-H with 4'-H; 3-H with 4-H.

$^{13}$C-NMR (75.43 MHz, $CDCl_3$, proton broadband-decoupled): d=168.84 (1C, C=O), 166.77 (1C, C=O), 139.37 (d, $^1J_{C,P}$=13.8 Hz, 1C, directly phosphorus-attached C atom of $C_6H_5$), 138.05 (d, $^1J_{C,P}$=13.8 Hz, 1C, directly phosphorus-attached C atom of $C_6H_5$), 134.40 (d, $^2J_{C,P}$=21.2 Hz, 1 C, ortho-C of $C_6H_5$), 133.24 (d, $^2J_{C,P}$=21.2 Hz, 1C, ortho'-C of $C_6H_5$), 128.76 (1C, para-C of $C_6H_5$), 128.24 (1 C, para'-C of $C_6H_5$), 128.14 (d, $J_{C,P}$=7.5 Hz, 2C, meta- and meta'-C of $C_6H_5$), 91.76 (d, $^2J_{C,P}$=21.7 Hz, 1C, C-2), 82.90 (1C, C-1'), 80.48 (d, $^1J_{C,P}$=14.3 Hz, 1C, C-1), 74.71 (1C, C-5), 73.41 (1C, C-4'), 73.34 (d, $^3J_{C,P}$=3.2 Hz, 1C, C-4), 72.15 (d, $^3J_{C,P}$=4.2 Hz, 1C, C-3), 71.85, 71.75 and 71.36 (respectively 1C, C-3',-2' and -5'), 50.01 (br, 2C, NCH), 45.88 (br, 2C, NCH), 21.15 and 20.34 (together 8C, $CH_3$). $^{31}$P-NMR (121.43 MHz, $CDCl_3$): d=−22.92. IR (KBr): n=2966, 1623 (C=O), 1320, 701 $cm^{-1}$. MS (FAB, NBA): m/z (%)=625 (100) [M+H$^+$], 624 (78) [M$^+$], 581 (33) [M$^+$-$CHMe_2$], 539 (48) ["581"-$CH_2$=CHMe]. UV (c=13.52 mg/ml in cyclohexane): $I_{max}$ (e)=220 nm (38480 I/mol·cm), 250 nm (12330), 440 nm (323).

Calculated for $C_{36}H_{45}FeN_2O_2P$ (624.59): C 69.23, H 7.26, Fe 8.94, N 4.49, P 4.96; found: C 69.4, H 7.0, Fe 8.7, N 4.3, P 5.2.

The absolute configuration of the title compound of the formula Ib corresponds to the configuration set out in the formula in Example 1. It is evident unambiguously from the single-crystal X-ray structural analysis of the corresponding compound of the formula Ia, which was carried out with the product of Example 4.

Example 2

1-(Diphenylphosphino)-1',2-bis(N,N-diisopropylamido) ferrocene (formula Ib, $R^1$:Ph, $(R^2)_2$:=O, $R^3$:iPr); preparation using 1.9 equivalents of n-BuLi and 2.0 equivalents of (−)-sparteine in diethyl ether

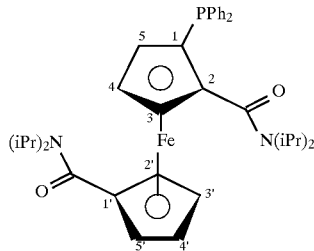

21.6 ml (34.5 mmol) of a 1.6 molar solution of n-butyllithium in hexane were added dropwise over the course of 5 minutes at −78° C., under argon and using a syringe, to a solution of 8.52 g (8.35 ml, 36.35 mmol) of (−)-sparteine in 100 ml of diethyl ether. The milky suspension was stirred at −78° C. for 20 minutes and then a solution of 8.00 g (18.16 mmol) of 1,1'-bis(N,N-diisopropylamido)-ferrocene in 250 ml of diethyl ether was added dropwise over the course of 15 minutes using a flex-needle, at a rate such that the internal temperature did not rise above −74° C. The solution, dark orange in color, was stirred under argon at −78° C. for 1 hour and then 9.80 ml (12.03 g, 54.5 mmol) of chlorodiphenylphosphine were added dropwise over the course of 10 minutes by syringe. After a reaction period of 10 minutes, a TLC sample was removed to which 0.5 ml of ether and 0.4 ml of saturated ammonium chloride solution were added, which sample, when analyzed with the eluent cyclohexane/ethyl acetate (3:1), showed virtually complete conversion. After a total reaction period of 30 minutes, the batch was heated to +4° C., and 200 ml of saturated ammonium chloride solution were added dropwise. The mixture was stirred for 15 minutes and then the phases were separated. In the separating funnel as well, argon was bubbled continuously through the liquid. In the case of the following extractions, phase mixing was regulated by the strength of the stream of argon that was passed through. The aqueous phase was extracted in this way with 2×100 ml of ether. The combined ethereal extracts were washed in the same way with 200 ml of saturated sodium chloride solution and then with 200 ml of water. The washed extracts were then evaporated to dryness in vacuo and the residue was dried in an HV. 16.5 g of an orange-brown, tough solid were obtained which, according to chiral phase HPLC analysis, contained product of 80% ee. The crude product was suspended in 200 ml of degassed diethyl ether and applied by flex-needle to a silica gel column (100 g of silica gel 60 Å, 65–70 mm). The suspension was pressed into the column with argon. It was then eluted with 500 ml of degassed diethyl ether. The product ran with the front and was collected together with less polar impurities. The solvent was immediately evaporated in vacuo and the residue dried in an HV. 14.8 g of orange-brown solid were obtained. This solid was dissolved in 300 ml of n-heptane by rapid heating to reflux while passing argon through it. The solution was cooled to room temperature, still with the passage of argon, to give 6.56 g (10.5 mmol, 58% of theory) of an orange-yellow powder which, according to chiral phase HPLC analysis, had 98% ee.

Example 3

1-(Diphenylphosphino)-1',2-bis(N,N-diisopropylamido) ferrocene (formula Ib, $R^1$:Ph, $(R^2)_2$:=O, $R^3$:iPr); preparation using 1.9 equivalents of n-BuLi and 2.0 equivalents of (−)-sparteine in toluene

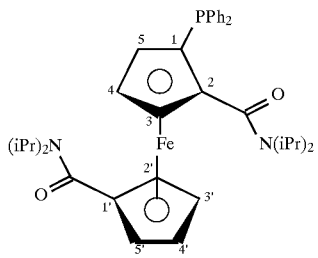

54 ml (86.3 mmol) of a 1.6 molar solution of n-butyllithium in hexane were added dropwise at from −73° to −78° C. under argon to a solution of 21.3 g (90.9 mmol) of (−)-sparteine in 40 ml of toluene (dried over 4 Å molecular sieve). The suspension was stirred at −78° C. for 20 minutes. Then a solution of 20.0 g (45.4 mmol) of 1,1'-bis(N,N-diisopropylamido)ferrocene in 140 ml of toluene were added dropwise at a rate such that the reaction temperature did not rise above −73° C. The mixture was stirred at −78° C. for 45 minutes and then 24 ml (133.7 mmol) of chlorodiphenylphosphine were added dropwise at a rate such that the internal temperature did not rise above −75° C. A TLC after a reaction period of 10 minutes showed virtually complete conversion to the monophosphine. After a reaction period of 30 minutes the solution was heated to +4° C., and 350 ml of saturated aqueous ammonium chloride solution were added dropwise. The phases were stirred together for 1 0 minutes and then the organic phase was separated off. The aqueous phase was subjected to extraction with 2×250 ml of toluene, during which argon was passed through. The combined toluene phases were washed with 400 ml of water and concentrated to dryness in vacuo. The resulting crude product had 91% ee according to chiral phase HPLC. It was suspended in 450 ml of Et$_2$O/toluene (1:1), pressed with argon into a column of 270 g of silica gel (35–70 mm), and eluted with 2 l of Et$_2$O. The eluate was concentrated to dryness and the residue was dried in a high vacuum. The orange-brown solid was recrystallized from 1.2 l of hot n-heptane while passing argon through it. 21.3 g (34.1 mmol, 75% of theory) were obtained of orange-yellow powder of 99% ee.

Example 4

$C_2$-symmetric 1,1'-bis(diphenylphosphino)-2,2'-bis(N,N-diisopropylamido)-ferrocene (formula Ia, $R^1$:Ph, $(R^2)_2$:=O, $R^3$:iPr); preparation from the corresponding monophosphine of the formula Ib using 2.1 equivalents of n-BuLi and 2.2 equivalents of (−)-sparteine

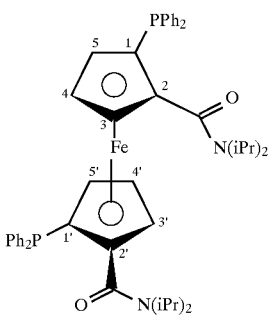

5.25 ml (8.4 mmol) of a 1.6 molar solution of n-butyllithium in hexane were added dropwise over the course of 5 minutes at −78° C. under argon to a degassed solution of 2.06 g (8.8 mmol) of (−)-sparteine in 70 ml of diethyl ether. During this addition, the internal temperature rose to not more than −74° C. The clear, pale yellow solution was stirred at −78° C. for 15 minutes, and then a solution of 2.50 g (4.0 mmol) of (+)-1-(diphenylphosphino)-1',2-bis(N,N-diisopropylamido)ferrocene (Example 1; 98.5% ee) in 30 ml of degassed diethyl ether was added dropwise over the course of 5 minutes at −78° C. In the weakly exothermic reaction, the internal temperature rose to not more than −74° C. The orange-colored suspension was stirred at −78° C. for 30 minutes and then 2.15 ml (2.65 g, 12.0 mmol) of chlorodiphenylphosphine were added over the course of 5 minutes using a syringe. As a result of the exothermic reaction the internal temperature rose to not more than −71° C. The mixture was subsequently stirred at −78° C. 15 and 30 minutes after the addition of chlorophosphine, samples (each 0.2 ml) were removed to which saturated ammonium chloride solution (each 0.2 ml) and $CH_2Cl_2$ (each 0.2 ml) were added. TLC analysis using the eluent toluene/ethyl acetate (15:1) showed substantial conversion, in the case of the first sample, and complete conversion, in the case of the second sample, of the starting material of the formula Ib ($R_f$=0.06) to the title compound of the formula Ia ($R_f$=0.20) and only traces of the meso-diphosphine of the formula II ($R_f$=0.24). 50 minutes after the addition of chlorophosphine the mixture was heated to room temperature, 100 ml of saturated aqueous ammonium chloride solution were added, and the mixture was subjected to extraction with 2×100 ml of dichloromethane. The extracts were immediately concentrated in vacuo. A 100 mg sample was taken from the residue for immediate analysis of the crude product by HPLC, $^1$H-NMR and $^{31}$P-NMR, while the remainder was flash-chromatographed immediately through a prepared column (100 g of silica gel) with the eluent toluene/ethyl acetate under 1.3 bar of nitrogen. This gave 1.79 g (2.21 mmol, 55% of theory) of yellow powder, m.p. (under argon in a fused capillary) 228°–230° C. (decomp.), $[a]_D^{20}$=+277.6° (c=0.76 in $CH_2Cl_2$), which had $^3$399% ee according to chiral phase HPLC analysis (250×4.6 mm CSP Chiralpak AD; eluent: n-hexane/iPrOH (87:13), flowrate 1.0 ml/min., 40° C., det. 233 nm; $t_{ret}$ (+)-title compound of the formula Ia 5.47 min.).

$^1$H-NMR (300 MHz, $CDCl_3$): d=7.15–7.37 (m, 20H, 4×$C_6H_5$), 4.80 (dt, $J_d$=2.5 Hz, $J_f$=1.2 Hz, 2H, 3-,3'-H), 4.71 (t, J=2.5 Hz, 2H, 4-,4'-H), 4.02 (br sept, J about 6 Hz, 2H, $CHMe_2$), 3.55 (m, 2H, 5-,5'-H), 3.18 (br sept, J about 6 Hz, 2H, $CHMe_2$), 1.41 (br d, J about 6 Hz, 6H, 2×$CH_3$), 1.08 (m, 12H, 4×$CH_3$), 0.57 (br d, J about 6 Hz, 6H, 2×$CH_3$).

$^{13}$C-NMR (75.43 MHz, $CDCl_3$, proton broadband-decoupled): d=167.09 (2C, C=O), 139.17 (d, $^1J_{C,P}$=14.3 Hz, 2C, directly phosphorus-attached C atom of $C_6H_5$), 138.06 (d, $^1J_{C,P}$=14.8 Hz, 2C, directly phosphorus-attached C atom of $C_6H_5$), 133.80 (d, $^2J_{C,P}$=20.7 Hz, 4C, o-C of $C_6H_5$), 133.37 (d, $2J_{C,P}$=21.2 Hz, 4C, o'-C of $C_6H_5$), 128.44 (2C, p-C of $C_6H_5$), 128.26 (2C, p'-C of $C_6H_5$), 128.10 (d, $^3J_{C,P}$=6.9 Hz, 4C, m-C of $C_6H_5$), 128.04 (d, $^3J_{C,P}$=6.3 Hz, 4C, m'-C of $C_6H_5$), 90.48 (d, $^2J_{C,P}$=18.0 Hz, 2C, C-2,2'), 81.32 (d, $^1J_{C,P}$=14.3 Hz, 2C, C-1,1'), 76.77 (2C, C-3,3'), 74.93 (d, $^3J_{C,P}$=6.4 Hz, 2C, C-4,4'), 72.70 (d, $^2J_{C,P}$=3.7 Hz, 2C, C-5,5'), 50.11 (2C, NCH), 45.88 (2C, NCH), 20.42 (8C, $CH_3$). $^{31}$P-NMR (121.43 MHz, $CDCl_3$): d=−22.00.

IR (KBr): n=2964, 1630 (C=O), 1444, 1328, 697 cm$^{-1}$.
MS (FAB, NBA): m/z (%)=809 (100) [M+H$^+$], 808 (97) [M$^+$], 765 (41) [M$^+$-iPr], 731 (14), 723 (12) ["765"-$CH_2$=CHMe]. UV (c=12.00 mg/ml in cyclohexane): $I_{max}$ (e)=223 nm (52760 I/molcm), 260 nm (14290), 445 nm (196).

Calculated for $C_{48}H_{54}FeP_2N_2O_2$ (808.77): C 71.29, H 6.73, N 3.46, P 7.66, Fe 6.91; found: C 70.8, H 6.5, N 3.2, P 7.4, Fe 6.5.

Single crystals of the title compound for X-ray structural analysis were obtained in a manner similar to that of Example 7 by the evaporation method ($CH_2Cl_2$/methyl tert-butyl ether). The crystallographic data were deposited at the Cambridge Crystallographic Data Centre, 12 Union Road, Cambridge CB2 1EZ. X-ray structural analysis confirms the structure. The absolute configuration determined for the title compound of the formula Ia corresponds to the configuration set out in the formula in Example 4. It is evident unambiguously from applying the Bijvoet method (J. M. Bijvoet, A. F. Peerdeman, A. J. van Bommel, Nature (London) 1951, 168, 271) to the single-crystal X-ray structural analysis data. From the X-ray structure it is inferred that the two ferrocene rings in the $C_2$-symmetric title compound of the formula Ia are virtually ecliptic in their configuration relative to one another. In contrast, the ferrocene rings in crystals of the corresponding meso compound (Example 7) are ideally staggered in their arrangement relative to one another.

HPLC analysis (250×4.6 mm CSP Chiralpak AD; eluent: n-hexane/iPrOH (87:13), flowrate 1.0 ml/min., 40° C., det. 233 nm; $t_{ret}$ (+)-title compound of the formula Ia 5.47 min, corresponding meso compound of the formula II (Example 7) 8.70 min) of the sample taken prior to flash chromatography of the crude product showed that the ratio of the compounds Ia to II was 97:3. The $^{31}$P resonance of the compound of the formula Ia was shifted downfield by Dd=0.38 ppm relative to that of the compound of the formula II. In the crude product, the ratio of intensity of the $^{31}$P resonances of the compounds Ia and II was 97.2:2.8. In addition, it was estimated from the $^1$H-NMR of the crude product that the contents of meso compound of the formula II is below 5%. Since the compound of the formula Ia is oxidized to the monophosphine oxide much faster than is the compound of the formula II, these analyses must be carried out immediately after sampling and using degassed solvents. $^{31}$P-NMR spectra of partially oxidized samples of the title compound of the formula Ia show two diastereomeric monophosphine oxides in a ratio of exactly 1:1, whose $Ph_2P$ resonances appear at d=−20.81 and −22.68 and whose $Ph_2PO$ resonances appear at d=+37.50 and +35.62, respectively.

Example 5

$C_2$-symmetric 1,1'-bis(diphenylphosphino)-2,2'-bis(N,N-diisopropylamido)-ferrocene (formula Ia, $R^1$:Ph, $(R^2)_2$:=O, $R^3$:iPr); preparation from the corresponding monophosphine of the formula Ib using 2.0 equivalents of n-BuLi and 2.1 equivalents of (−)-sparteine, with improved workup and purification of the product without chromatography

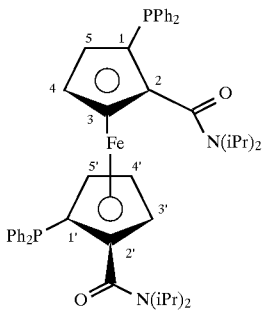

15.00 ml (24.0 mmol) of a 1.6 molar solution of n-butyllithium in hexane were added dropwise at −78° C. by syringe to a solution of 5.92 g (5.80 ml, 25.2 mmol) of (−)-sparteine in 30 ml of diethyl ether, and the mixture was stirred at −78° C. for 20 minutes. A solution of 7.46 g (11.94 mmol) of (+)-1-(diphenylphosphino)-1',2-bis(N,N-diisopropylamido)ferrocene (98% ee) in 190 ml of diethyl ether was then added dropwise by flex-needle at a rate such that the internal temperature did not rise above −77° C. Stirring was continued at −78° C. for 1 hour and then 4.00 ml of chlorodiphenylphosphine were added dropwise by syringe over the course of 5 minutes. TLC after a reaction period of 10 minutes showed virtually complete conversion to the diphosphine. After 30 minutes, the cooling bath was removed and the orange-colored suspension was warmed to +3° C. Subsequently, 150 ml of half-concentrated aqueous ammonium chloride solution were added dropwise, and the two-phase mixture was stirred intensely for 10 minutes. Even at this stage a yellow precipitate was formed. For more complete precipitation of the product, 200 ml of n-pentane were added. The precipitate was filtered off with suction, washed with n-pentane and dried in an HV. This gave 6.23 g (7.70 mmol, 65% of theory) of yellow crystals of 100% ee and >99% chemical purity (chiral phase HPLC). Immediate concentration of the mother liquor in vacuo and trituration of the residue with n-pentane gave a further 0.82 g, which consisted of 75% of the title compound of the formula Ia and 25% of the corresponding meso-diphosphine of the formula II.

Example 6

$C_2$-symmetric 1,1'-bis(diphenylphosphino)-2,2'-bis(N,N-diisopropylamido)-ferrocene (formula Ia, $R^1$:Ph, $(R^2)_2$:═O, $R^3$:iPr); preparation from the racemate of the corresponding monophosphine of the formula rac-Ib using 2.1 equivalents of n-BuLi and 2.2 equivalents of (−)-sparteine and with separation of the corresponding meso-diphosphine of the formula II.

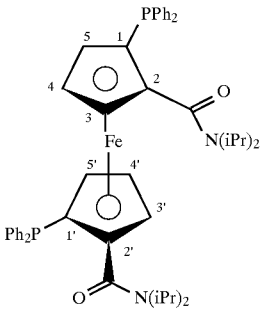

Racemic 1-(diphenylphosphino)-1',2-bis(N,N-diisopropylamido)ferrocene was prepared by lithiating 1,1'-bis(N,N-diisopropylamido)ferrocene with 4.45 equivalents of N,N,N',N'-tetramethylethylenediamine (TMEDA) and 4.40 equivalents of n-BuLi in $Et_2O$ at −78° C., followed by the addition of 6.0 equivalents of chlorodiphenylphosphine and workup as in Example 1, in a yield of 50%.

7.6 ml (12.1 mmol) of a 1.6 molar solution of n-butyllithium in hexane were added dropwise at −78° C. to a solution of 3.0 g (12.8 mmol) of (−)-sparteine in 84 ml of diethyl ether. After 15 minutes, a solution of 3.6 g (5.76 mmol) of racemic 1-(diphenylphosphino)-1',2-bis(N,N-diisopropylamido)ferrocene in 60 ml of diethyl ether was added dropwise at −78° C. over the course of 5 minutes. The clear, red-brown solution was stirred at −78° C. for 1 hour and then 3.1 ml (3.82 g, 17.3 mmol) of chlorodiphenylphosphine were added dropwise over 5 minutes. A TLC sample after 30 minutes showed complete conversion of the starting material. After a total reaction period of 1 hour the mixture was heated to 20° C., 150 ml of saturated ammonium chloride solution were added dropwise, and the mixture was stirred vigorously for 5 minutes. Workup was as described in Example 5. The crude product (8.0 g of brown, amorphous solid) contained the $C_2$-symmetric diphosphine of the formula Ia and the corresponding meso-diphosphine of the formula II in a ratio of about 1:1 (TLC). Flash chromatography was carried out with the eluent toluene/ethyl acetate (15:1) through 200 g of silica gel (35–70 mm), in the course of which the relatively apolar meso-diphosphine of the formula II was separated and the pure title compound of the formula Ia was collected. 1.95 g (2.41 mmol, 40% of theory) of yellow solid of the title compound Ia of >99%ee and 2.20 g (2.72 mmol, 46% of theory) of a light brown solid were obtained, the solid consisting in accordance with chiral phase HPLC predominantly of the corresponding meso-diphosphine of the formula II and 30% of the $C_2$-symmetric diphosphine of the formula Ia of 99% ee.

Example 7 meso-1,1'-Bis(diphenylphosphino)-2,2'-bis(N,N-diisopropylamido)ferrocene (formula II, $R^1$:Ph, $(R^2)_2$:═O, $R^3$:iPr); preparation using 4.40 equivalents of sec-BuLi and 4.45 equivalents of (−)-sparteine

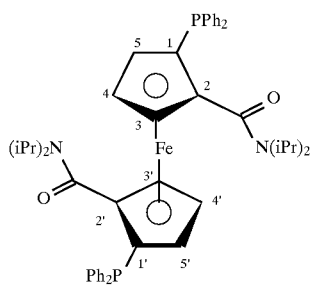

11.5 ml (15.0 mmol) of a 1.3 molar solution of sec-butyllithium in cyclohexane were added dropwise over the course of 10 minutes at −78° C. and under argon to a solution of 3.56 g (3.5 ml, 15.17 mmol) of (−)-sparteine and 65 ml of diethyl ether. The mixture was stirred at −78° C. for 15 minutes and then a solution of 1.50 g of 1,1'-bis(N,N-diisopropylamido)ferrocene (3.41 mmol) in 27 ml of diethyl ether was added dropwise over the course of 10 minutes. The mixture was stirred at −78° C. under argon for 2 hours. Using a syringe, 3.7 ml (4.51 g, 20.4 mmol) of chlorodiphenylphosphine were added dropwise over the course of 10 minutes. During this addition, the previously brown, clear solution underwent a color change first of all to deep brown and then to virtually black. After the end of the addition, this dark solution turned into an orange-colored suspension. After stirring at −78° C. for 30 minutes, a TLC sample (0.5 ml) was taken, saturated ammonium chloride solution (0.5 ml) and Et$_2$O (0.5 ml) were added, and TLC analysis was carried out with the eluent cyclohexane/ethyl acetate (3:1). Reaction was virtually complete (product: R$_f$=0.45). The corresponding monophosphine of the formula Ib (cf. Example 1; R$_f$=0.27) and the starting material of the formula III (R$_f$=0.13) were detectable only in slight traces. The mixture was stirred for a further 30 minutes and warmed to room temperature. Then 80 ml of saturated ammonium chloride solution were added dropwise over the course of 5 minutes and the mixture was stirred for a further 15 minutes. The yellow solid was filtered off with suction from the two-phase suspension, stirred with 10 ml of water and again subjected to suction filtration, before being washed with 10 ml of ether and dried in an HV (1.9 g of yellow solid, homogeneous in the above TLC eluent; in toluene/ethyl acetate (10:1) it is evident that there is, in addition to the product (R$_f$=0.33), about 4–5% of the isomer of the formula Ia (R$_f$=0.29)). Immediate subjection of the filtrate to extraction with 2×50 ml of methylene chloride, washing of the combined extracts with water (50 ml) and sodium chloride solution (50 ml) followed by concentration in vacuo and trituration of the residue with ether gave a further 0.45 g of yellow solid which had a purity of about 90% according to TLC and NMR, still with a content of diphosphine of the formula Ia of 4–5%. Overall yield: 2.35 g (2.91 mmol, 85% of theory), m.p. 223°–224° C. (decomp.), $[a]_D^{20}$=+4.3° (c=0.74 in CH$_2$Cl$_2$).

$^1$H-NMR (300 MHz, CDCl$_3$): d=7.57 (m, 4H, pH of C$_6$H$_5$), 7.10–7.37 (m, 16H, o- and m-H of C$_6$H$_5$), 4.74 (s, 2H, 3-,3'-H), 4.20 and 4.19 (2×s, 4H, 4-,4'-,5-,5'-H), 3.79 (br s, 2H, CHMe$_2$), 3.11 (brs, 2H, CHMe$_2$), 1.25–0.70 (m, 18H, CH$_3$), 0.50 (brs, 6H, CH$_3$).

$^{13}$C-NMR (75.43 MHz, CDCl$_3$, proton broadband-decoupled): d=166.36 (2C, C=O), 139.78 (d, $^1J_{C,P}$=13.3 Hz, 2C, directly phosphorus-attached C atoms of C$_6$H$_5$), 138.25 (d, $^1J_{C,P}$=13.7 Hz, 2C, directly phosphorus-attached C atoms of C$_6$H$_5$), 134.75 (d, $^2J_{C,P}$=22.8 Hz, 2C, ortho-C of C$_6$H$_5$), 132.98 (d, $^2J_{C,P}$=20.6 Hz, 2C, ortho-C of C$_6$H$_5$), 128.89 (2C, para-C of C$_6$H$_5$), 128.14 (d, $^3J_{C,P}$=7.8 Hz, 4C, meta-C of C$_6$H$_5$), 128.05 (2C, para-C of C$_6$H$_5$), 91.07 (d, $^2J_{C,P}$=21.2 Hz, 2C, C-2,2'), 81.30 (d, $^1J_{C,P}$=13.7 Hz, 2C, C-1,1'), 75.41 (2C, C-5,5' or C-4,4'), 74.77 (d, J$_{C,P}$=4 Hz, 2C, C-4,4' or C-5,5'), 72.86 (d, $^3J_{C,P}$=4 Hz, 2C, C-3,3'), 49.94 (br, 2C, NCH), 45.78 (br, 2C, NCH), 20.36 (8C, CH$_3$).
$^{31}$P-NMR (121.43 MHz, CDCl$_3$): d=−22.38 (2 isochronic P atoms).

IR (KBr): n=3068 (aryl-H), 2964, 1632 (C=O), 1455, 1335, 1283, 823, 740, 696 cm$^{-1}$. MS (FAB, NBA/LiCl): m/z (%)=815 (100) [M+Li$^+$], 809 (70) [M+H$^+$], 765 (40) [M$^+$-iPr], 723 (15) ["765"-CH$_2$=CHMe]. UV (c=14.84 mg/ml in cyclohexane): I$_{max}$ (e)=223 nm (47960 I/mol cm), 250 nm (16350), 445 nm (327).

HPLC analysis (CSP Chiralpak AD) showed a ratio of the compounds of the formulae II and Ia of 96.4:3.6. X-ray powder diffraction of this solid likewise showed traces of the compound of the formula Ia as an impurity. Isomer-free, analytically pure crystals for single-crystal X-ray structural analysis and elemental analysis of the meso-diphosphine of the formula II were obtained by recrystallization from methyl tert-butyl ether/dichloromethane by the evaporation method. For this purpose, 100 mg of the above product were suspended in 7 ml of degassed methyl tert-butyl ether, and degassed dichloromethane was added dropwise until a clear solution was present. This solution was left to stand in the dark for 2 days in an open flask in a large, argon-filled, sealed desiccator. Evaporation of the dichloromethane caused the solution to become supersaturated, and large crystals formed. The mother liquor was decanted off and the crystals were washed with freshly distilled Et$_2$O. The sample fractions for elemental analysis, optical rotation and melting point were dried intensely in an HV. The crystals for X-ray structural analysis and repetition of the X-ray powder diffraction were not dried. m.p. 229°–231° C. (decomp.), $[a]_D^{20}$=0° (c=1 in CH$_2$Cl$_2$); calculated for C$_{48}$H$_{54}$FeP$_2$N$_2$O$_2$ (808.77): C 71.29, H 6.73, N 3.46, P 7.66, Fe 6.91; found: C 70.9, H 6.6, N 3.3, P 7.4, Fe 6.3. In the X-ray powder diffractogram and in TLC, the isomeric compound of the formula Ia could now no longer be detected. Single-crystal X-ray structural analysis confirms the structure of the title compound. The crystallographic data were deposited at the Cambridge Crystallographic Data Centre, 2 Union Road, Cambridge CB2 1EZ. The two ferrocene rings are ideally staggered in their arrangement with respect to one another. The compound is in the conformation indicated in the formula in Example 7.

Example 8 meso-1,1'-Bis(diphenylphosphino)-2,2'-bis(N,N-diisopropylamido)ferrocene (formula II, R$^1$:Ph, (R$^2$)$_2$:=O, R$^3$:iPr); preparation using 3.00 equivalents of sec-BuLi and 3.05 equivalents of (−)-sparteine

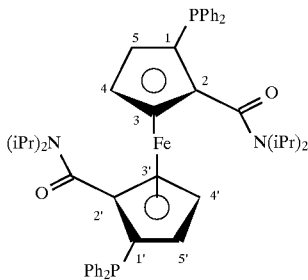

A batch analogous to Example 7 in Et₂O (65 ml/g 1,1'-bis(N,N-diisopropyl-amido)ferrocene), but with a reduced amount of the chiral lithium base (3.00 equivalents of sec-BuLi, 3.05 equivalents of (−)-sparteine), gave, with an unchanged lithiation period (2.0 hours at −74° to −78° C.) and with a reduced amount of chlorodiphenylphosphine (4.00 equivalents), the title product in a yield of 76% of theory. The diastereoselectivity was unchanged relative to Example 7.

Example 9 meso-1,1'-Bis(diphenylphosphino)-2,2'-bis(N,N-diisopropylamido)ferrocene (formula II, $R^1$:Ph, $(R^2)_2$:=O, $R^3$:iPr); preparation using 3.00 equivalents of sec-BuLi and 3.05 equivalents of N,N ,N',N'-tetramethylethylenediamine (TMEDA)

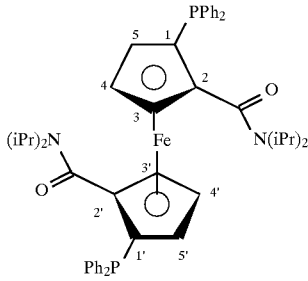

A batch analogous to Example 8 but with TMEDA instead of (−)-sparteine, gave the title product in a yield of 64% of theory. The diastereoselectivity was unchanged relative to Examples 7 and 8.

Example 10

Palladium dichloride complex of the C₂-symmetric 1,1'-bis(diphenylphosphino)-2,2'-bis(N,N-diisopropylamido)ferrocene (formula Ia×PdCl₂, $R^1$:Ph, $(R^2)_2$:=O, $R^3$:iPr); preparation from the corresponding homochiral diphosphine of the formula Ia and bis(acetonitrile)palladium(II) chloride ($(CH_3CN)_2PdCl_2$)

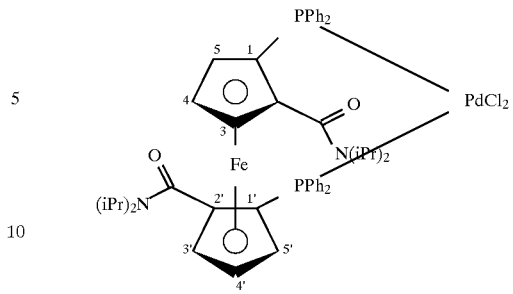

To a suspension of 195 mg (0.75 mmol) of bis (acetonitrile)palladium(II) chloride (Fluka) in 8 ml of degassed dry toluene and 6 ml of degassed dry dichloromethane there were added, at room temperature (22° C.) and in one portion, 606 mg (0.75 mmol) of crystalline, homochiral C₂-symmetric 1,1'-bis(diphenylphosphino)-2,2'-bis(N,N-diisopropylamido)ferrocene (from Example 5). Further dichloromethane (7 ml) was added to the suspension until a clear solution was obtained. TLC (eluent toluene/ ethyl acetate (10:1)) after 30 minutes indicated complete reaction of the diphosphine of the formula Ia. 40 ml of degassed n-pentane were added to the solution, and the precipitate was filtered off with suction and washed with n-pentane. Drying in HV gave 660 mg (0.67 mmol, 89% of theory) of an orange-brown powder, m.p. (under argon in a fused capillary) 265° C. (decomp.; black coloration from 230° C.), $[a]_D^{20}$=−484.0° (c=0.505 in $CH_2Cl_2$). According to ¹H-NMR, ¹³C-NMR and ³¹P-NMR this powder contained, other than traces of toluene, no impurities and was 99.2% pure according to HPLC analysis (125×4 mm SP Purospher 5 mm; eluent $CH_3CN$/water (40:30) plus 0.3% $KH_2PO_4$ plus 0.1% camphorsulfonic acid; flowrate 1.0 ml/min; 40° C.; det. 216 nm; $t_{ret}$ of the title compound 8.95 min).

¹H-NMR (300 MHz, $CD_2Cl_2$): d=8.61 (br s, 4H, arom. H), 8.15 (m, 4H, arom. H), 7.30–7.50 (m, 12H, arom. H), 4.35 (s, 2H, ferrocenyl-H), 4.30 (s, 4H, ferrocenyl-H), 3.92 (sept, J=6.5 Hz, 2H, $CHMe_2$), 3.08 (sept, J=6.5 Hz, 2H, $CHMe_2$), 1.07 (d, J ca. 6.5 Hz, 6H, 2×$CH_3$), 1.03 (d, J ca. 6.5 Hz, 12H, 4×$CH_3$), 0.76 (d, J=6.5 Hz, 6H, 2×$CH_3$).

¹³C-NMR (75.43 MHz, $CD_2Cl_2$, proton broadband-decoupled; multiplicity confirmed with DEPT 135° ): d=166.99 (2C, C=O), 136.76 (d, $^4J_{C,P}$=4.7 Hz, 2C, p-C of $C_6H_5$), 136.69 (d, $^4J_{C,P}$=5.3 Hz, 2C, p'-C of $C_6H_5$), 135.49 (d, $^1J_{C,P}$=26.0 Hz, 2C, directly phosphorus-attached C atoms of $C_6H_5$), 134.81 (d, $^1J_{C,P}$=26.0 Hz, 2C, directly phosphorus-attached C atoms of $C_6H_5$), 130.15 (d, $^2J_{C,P}$= 19.1 Hz, 2C, o- and o'-C of $C_6H_5$), 127.52 (d, $^3J_{C,P}$=5.8 Hz, 2C, m'-C of $C_6H_5$), 127.44 (d, $^3J_{C,P}$=5.8 Hz, 4C, m-C of $C_6H_5$), 127.37 (d, $^3J_{C,P}$=5.9 Hz, 2C, m'-C of $C_6H_5$), 98.92 (d, $^1J_{C,P}$=29.1 Hz, 2C, C-1,1'), 98.53 (d, $^2J_{C,P}$=29.7 Hz, 2C, C-2,2'), 86.46 (2C, C-3,3'), 70.01 (2C, C-4,4'), 68.29 (2C, C-5,5'), 50.18 (2C, NCH), 46.76 (2C, NCH), 21.74 (4C, $CH_3$), 20.40 (2C, $CH_3$), 20.22 (2C, $CH_3$). ³¹P-NMR (121.43 MHz, $CD_2Cl_2$): d=+50.03.

IR (KBr): n=3054, 2967, 1612 (C=O), 1436, 1332, 693 cm⁻¹. MS (FAB, NBA): m/z (%)=990 (1), 989 (2), 988 (4), 987 (4), 986 (6), 985 (4), 984 (5), 983 (4), 982 (2) (peak series for [M+H+]); 956 (7), 955 (15), 954 (27), 953 (55), 952 (48), 951 (96), 950 (62), 949 (100), 948 (63), 947 (30), 946 (5) (peak series for M-Cl; Intensity ratio agrees with isotope simulation for $C_{48}H_{54}FeP_2N_2O_2PdCl$); 919 (4), 918 (7), 917 (8), 916 (14), 915 (10), 914 (19), 913 (13), 912 (6) (peak series for M-2Cl); 376 (66) (c-$C_5H_3(PPh_2)(CONiPr_2)$ +); 292 (42).

To prepare single crystals for X-ray structural analysis, a crystallizing dish was rinsed out twice with 5 ml of hexamethyldisilazane each time, rinsed once with methanol and dried in air. 40 mg of the complex were dissolved in 20 ml of degassed dichloromethane in the crystallizing dish and were placed together with a crystallizing dish containing 10 ml of degassed n-heptane in an argon-filled desiccator. Crystals formed over the course of 2 days. The solvent was decanted off, the crystals were washed with n-heptane and dried in a stream of argon, and one good crystal was fused into a Mark tube and measured. The crystallographic data were deposited at the Cambridge Crystallographic Data Centre, 12 Union Road, Cambridge CB2 1EZ. The result of the X-ray structural analysis confirms the structure of the title complex. It is noted that the coordination sphere around the palladium atom is substantially square-planar. The two ferrocenyl rings are arranged almost ecliptically and the two phosphino groups are almost directly behind one another in plan view. In the crystal lattice, the $C_2$ symmetry is also retained conformatively. A solvate is present, with dichloromethane incorporated into the crystal lattice.

Example 11

1,5-Cyclooctadiene-rhodium(I) tetrafluoroborate complex of the $C_2$-symmetric 1,1'-bis(diphenylphosphino)-2,2'-bis(N,N-diisopropylamido)ferrocene (formula [Ia×(COD)Rh(I)]$^+$BF$_4^-$, R$^1$:Ph, (R$^2$)$_2$:=O, R$^3$:iPr); preparation from the corresponding homochiral diphosphine of the formula Ia and bis(1,5-cyclooctadiene)rhodium(I) tetrafluoroborate ([Rh(I)(COD)$_2$]$^+$BF$_4^-$)

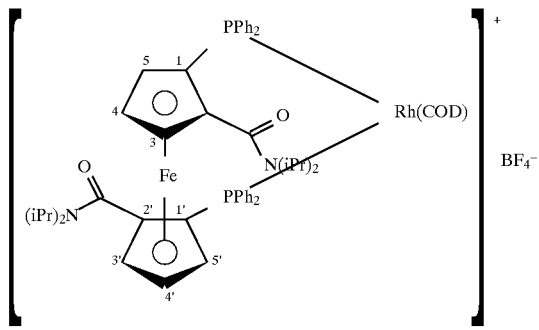

To a clear brown solution of 100 mg (0.246 mmol) of bis(1,5-cyclooctadiene)rhodium(I) tetrafluoroborate in 10 ml of degassed dichloromethane there were added, at room temperature and in one portion, 197 mg (0.246 mmol) of crystalline homochiral $C_2$-symmetric 1,1'-bis(diphenylphosphino)-2,2'-bis(N,N-diisopropylamido) ferrocene (from Example 5), during which a color change to orange took place. TLC (silica gel; eluent dichloromethane/methanol (5:1)) of the reaction mixture after 10 minutes showed complete conversion of the compound of the formula Ia ($R_f$=0.94) and of [Rh(COD)$_2$]BF$_4$ ($R_f$=0.00) to the product ($R_f$=0.70). After 30 minutes the mixture was concentrated to dryness in vacuo. The residue is dissolved in 3 ml of methanol and the product was precipitated by adding 30 ml of ether, filtered off with suction, washed with 10 ml of ether and dried in vacuo. Yield was 186 mg (68% of theory) of yellow powder, m.p. (under argon in a fused capillary) 225° C. (decomp.; black coloration at 150°–190° C.), $[\alpha]_D^{20}$=+156° (c=0.125 in CH$_2$Cl$_2$).

$^1$H-NMR (500 MHz, CDCl$_3$): d=7.80–6.70 (m, 20H, 4×C$_6$H$_5$), 5.49 (br s, 2H, =CH of COD), 4.86 (br s, 2H, =CH of COD), 3.85–4.70 (m, 2H, 3-, 3'-H), 3.40 (br s, 2H, 2×CHMe$_2$), 3.30 (br s, 1 H, 4-H), 3.00 (br s, 1 H, 4'-H), 2.70 (br s, 1 H, 5-H), 2.53 (br s, 1H, 5'-H), 2.20–2.42 (m, 6H, 2×CH$_2$ of COD and 2×CHMe$_2$), 1.98 (br s, 2H, CH$_2$ of COD), 1.75 (br s, 2H, CH$_2$ of COD), 1.25 (m, 6H, CH$_3$), 0.95–1.22 (m, 12H, CH$_3$), 0.30–0.80 (m, 6H, CH$_3$).

$^{13}$C-NMR (125.77 MHz, CDCl$_3$, proton broadband-decoupled): d=170.74 (2C, C=O), 134.16 and 134.05 (2×s or 1×d, 4C, arom. C), 131.36 (s, 4C, arom. C), 131.12 (s, 4C, arom. C), 131.02 and 130.94 (2×s or 1×d, 4C, arom. C), 128.84 and 128.76 (2×s or 1×d, 4C, arom. C), 128.52 and 128.44 (2×s or 1×d, 4C, arom. C), 108.70 (br s, 2C, =C of COD), 107.83 (br s, 2C, =C of COD), 81.86 (s, 2C, C-2,2'), 78.07 (s, 2C, C-1,1'), 74.69 (s, 2C, C-3,3'), 69.48 (s, 2C, C-4,4'), 66.23 (s, 2C, C-5,5'), 52.73 (s, 1 C, NCH), 47.38 (s, 1 C, NCH), 34.22 (s, 1 C, CH$_2$ of COD), 29.87 (s, 1 C, CH$_2$ of COD), 28.06 (s, 1C, CH$_2$ of COD), 25.84 (s, 1C, CH$_2$ of COD), 19.35 (s, 2C, CH$_3$), 19.23 (s, 4C, CH$_3$), 18.96 (s, 2C, CH$_3$). $^{31}$P-NMR (161.98 MHz, CDCl$_3$): d=+24.20 (d, $^1J_{P,Rh}$=149.6 Hz; two isochronic P atoms, i.e. $C_2$-symmetry retained).

IR (KBr): n=2971, 1628 (C=C or C=O), 1548 (N-C=O), 1437, 1370, 1055, 697, 520 cm$^{-1}$. MS (FAB, NBA): m/z (%)=1022 (6), 1021 (22), 1020 (66), 1019 (100), 1018 (4), 1017 (7) (peak series for M$^+$ of the cation (M-BF$_4^-$); intensity ratio identical with isotope simulation for C$_{56}$H$_{66}$FeP$_2$N$_2$O$_2$Rh); 913 (16), 912 (51), 911 (83), 910 (7), 909 (7) (peak series for M-BF$_4^-$-COD).

Example 12

Ruthenium(II) iodide-cumene complex of the $C_2$-symmetric 1,1'-bis(diphenylphosphino)-2,2'-bis(N,N-diisopropylamido)ferrocene (formula Ia×RuI$_2$×p-Me$_2$CH—C$_6$H$_4$—Me, R$^1$:Ph, (R$^2$)$_2$:=O, R$^3$:iPr); preparation from the corresponding homochiral diphosphine of the formula Ia and [p-cumene-ruthenium diiodide] dimer

[p-Cumene-ruthenium diiodide] dimer was prepared by the method of K. Mashima et al., J. Chem. Soc., Chem. Commun. 1989,1208 as a purple-brown solid from ruthenium(III) chloride trihydrate, (R)-(–)-a-phellandrene and potassium iodide in aqueous ethanol. 91 mg (0.0927 mmol) of this complex and 150 mg (0.185 mmol) of crystalline homochiral 1,1'-bis(diphenylphosphino)-2,2'-bis(N,N-diisopropyl-amido)ferrocene (from Example 5) were dissolved in 8 ml of dichloromethane and the dark solution was stirred at room temperature. TLC (dichloromethane/methanol (15:1)) after 10 minutes indicated complete conversion of the ruthenium complex and substantial conversion of the diphosphine of the formula Ia. After 1 hour the solvent was removed in vacuo, the residue was taken up in 3 ml of dichloromethane and the product was precipitated by adding 20 ml of diethyl ether. It was filtered off with suction, washed with ether and dried in a high vacuum. Yield was 174 mg of light brown powder (0.134 mmol, 73% of theory), m.p. –190° C. (decomp.; black coloration from 145° C.), $[\alpha]_D^{20}$=+280° (c=0.1 in CH$_2$Cl$_2$). The precipitated product is homogeneous according to TLC ($R_f$=0.30) and free diphosphine of the formula Ia ($R_f$=0.94) can no longer be detected. $^1$H-NMR and $^{31}$P-NMR spectra of this product in CDCl$_3$ are highly complex and do not alter when the NMR solution is left to stand. NMR spectra in toluene-d$_8$ or benzene-d$_6$ are likewise highly complex straight after the sample has been dissolved, but simplify increasingly when the NMR solution is left to stand at room temperature, and give an interpretable spectrum after 4 days: $^{31}$P-NMR (161.98 MHz, toluene-d$_8$): only one remaining singlet at d=+22.43; two isochronic P atoms, i.e. $C_2$ symmetry retained and no tetrahedral ligand arrangement around the ruthenium.

31

The $^1$H-NMR shows two sets of signals for the isopropyl group and the methyl group of the cumene ligand, which points to the presence of two conformers (ratio 1.6:1) of the cumene ligand. $^1$H-NMR (400 MHz, toluene-d$_8$): d=7.75 (m, 4H, C$_6$H$_5$), 7.10 (t, 8H, C$_6$H$_5$), 7.02 (t, 4H, C$_6$H$_5$), 6.98 (t, 3H, C$_6$H$_5$), 5.61 (br s, 2H, arom. H of cumene), 5.36 (br s, 2H, arom. H of cumene), 5.00 (d, $^3J_{H,P}$=5.8 Hz, 1H, 5-H), 4.83 (d, $^3J_{H,P}$=5.8 Hz, 1 H, 5'-H), 3.92 (br s, 2H, 3,3'-H), 3.84 (br s, 2H, NCH), 2.95 (br s, 2H, NCH), 2.86 and 2.72 (2×sept, $^3J_{H,H}$=7 Hz, together 1 H, Me$_2$CH-Aryl, 2 conformers), 2.16 (s, 2H, 4,4'-H), 2.08 and 1.95 (2×s, together 3H, CH$_3$-Aryl, 2 conformers), 1.47 (br d, 6H, CH$_3$), 1.27 (br d, 6H, CH$_3$), 1.17 and 1.00 (2×d, $^3J_{H,H}$=7 Hz, together 6H, (CH$_3$)$_2$CH-Aryl, 2 conformers), 0.85 (br d, 6H, CH$_3$), 0.48 (br d, 6H, CH$_3$).

IR (KBr): n=1625, 1539, 1438, 1370, 1328, 699 cm$^{-1}$. MS (FBA, CH$_2$Cl$_2$, NBA): m/z (%)=1175 (10), 1174 (30), 1173 (58), 1172 (56), 1171 (100), 1170 (62), 1169 (53), 1168 (32), 1167 (9), 1166 (9) (peak series for M$^+$ of the cation [iPrC$_6$H$_4$Me×RuI×Ia]$^+$; intensity ratio identical with isotope simulation for C$_{58}$H$_{68}$FeP$_2$N$_2$O$_2$IRu).

Example 13

1,5-Cyclooctadiene-iridium(I) chloride complex of the C$_2$-symmetric 1,1'-bis(diphenylphosphino)-2,2'-bis(N,N-diisopropylamido)ferrocene (formula [Ia×Ir(I)(COD)Cl]; R$^1$:Ph, (R$^2$)$_2$:=O, R$^3$; iPr); preparation from the corresponding homochiral diphosphine of the formula Ia and [chloro (1,5-cyclooctadiene)iridium(I)] dimer ([Ir(I)(COD)Cl]$_2$)

297 mg (0.44 mmol) of [chloro(1,5-cyclooctadiene) iridium(I)] dimer (Strem Chemicals) and 716 mg (0.89 mmol) of crystalline homochiral 1,1'-bis (diphenylphosphino)-2,2'-bis(N,N-diisopropylamido) ferrocene (from Example 5) were dissolved in 40 ml of dichloromethane which had been freed beforehand from dissolved oxygen by bubbling argon through it. The clear solution was stirred at 20° C. under argon for 15 minutes. The solvent was removed in vacuo and the residue was dried in a high vacuum. This gave 1.01 g (100% of theory) of orange-colored powder.

$^1$H-NMR (250 MHz, CDCl$_3$): d=7.91 (br s, 4H, arom. H), 7.70 (br s, 4H, arom. H), 7.28–7.52 (m, 12H, arom. H), 4.40–4.87 (m, 6H, 2 =CH of COD, 4 ferrocenyl-H), 4.14 (br s, 4H, 2 =CH of COD, 2 ferrocenyl-H), 3.30 (br s, 2H, NCH), 3.15 (br s, 2H, NCH), 2.47 (m, 2H, CH$_2$ of COD), 2.01 (m, 2H, CH$_2$ of COD), 1.58–1.79 (m, 4H, CH$_2$ of COD), 1.36 (d, 6H, CH$_3$), 1.25 (br s, 6H, CH$_3$), 1.15 (d, 6H, CH$_3$), 0.96 (br s, 6H, CH$_3$). $^{31}$P-NMR (161.98 MHz, CDCl$_3$): d=+21.60 (singlet, mid-peak width 106 Hz). MS (FAB, NBA): m/z (%)=1112 (5), 1111 (19), 1110 (60), 1109 (100), 1108 (38), 1107 (58), 1106 (2), 1105 (3) (peak series for M-Cl; intensity ratio in agreement with isotope simulation for C$_{56}$H$_{66}$FeP$_2$N$_2$O$_2$Ir); 1003 (5), 1002 (12), 1001 (14), 1000 (12), 999 (13), 998 (4), 997 (4) (peak series for M-Cl-COD).

32

We claim:
1. A compound of the formula I

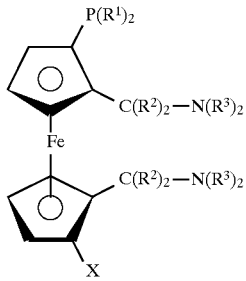

in which the substituents R$^1$ are cyclohexyl, unsubstituted phenyl C$_6$H$_5$ or substituted phenyl C$_6$H$_{5-n}$R$^4{}_n$ where n is 1 to 5 and the substituents R$^4$ are unbranched or branched C$_1$- to C$_4$-alkyl, C$_1$- to C$_4$-alkoxy or halogen;

the two geminal substituents R$^2$ together are a doubly bonded oxygen atom (i.e. (R$^2$)$_2$ is =O) or each substituent R$^2$ on its own is hydrogen;

the substituents R$^3$, each on their own, are unbranched or branched C$_1$- to C$_4$-alkyl, cyclopentyl, cyclohexyl, unsubstituted phenyl C$_6$H$_5$ or substituted phenyl C$_6$H$_{5-n}$R$^4{}_n$, where n and R$^4$ are as defined above under R$^1$, or the substituents R$^3$ are connected to one another to form a ring, in which case together they are tetramethylene —(CH$_2$)$_4$—, pentamethylene —(CH$_2$)$_5$—, 3-oxapentamethylene —(CH$_2$)$_2$—O—(CH$_2$)$_2$— or N-methyl-3-azapentamethylene —(CH$_2$)$_2$—N(CH$_3$)—(CH$_2$)$_2$—;

the substituent X is hydrogen or P(R$^1$)$_2$;

or a salt thereof.

2. A compound of the formula I as claimed in claim 1, in which the substituents R$^1$ are cyclohexyl, phenyl, p-tolyl, p-tert-butylphenyl or p-halophenyl, in which case halogen here is fluorine, chlorine or bromine; the two substituents R$^2$ together are a doubly bonded oxygen atom (i.e. (R$^2$)$_2$ is=O) or each substituent R$^2$ by itself is hydrogen;

the substituents R$^3$ are isopropyl, cyclohexyl or phenyl, or the two substituents R$^3$ together are —(CH$_2$)$_4$—, —(CH$_2$)$_5$—, —(CH$_2$)$_2$—O—(CH$_2$)$_2$— or —(CH$_2$)$_2$—N(CH$_3$)—(CH$_2$)$_2$—;

the substituent X is hydrogen or P(R$^1$)$_2$ in which R$^1$ is cyclohexyl, phenyl, p-tolyl, p-tert-butylphenyl or p-halophenyl and halogen in this case is fluorine, chlorine or bromine.

3. A compound of the formula I as claimed in claim 2, in which R$^1$ is phenyl, the two substituents R together are a doubly bonded oxygen atom, R$^3$ is isopropyl and X is hydrogen or P(phenyl)$_2$.

4. A compound of the formula I as claimed in one or more of claims 1 to 3 in optically active form.

5. A compound of the formula I as claimed in one or more of claims 1 to 3 in racemic form.

6. A process for preparing an optically active monophosphine of the formula I as claimed in claim 1, in which the radicals R$^1$, R$^2$ and R$^3$ are as defined in claim 1 and X is hydrogen, which comprises subjecting a compound of the formula III,

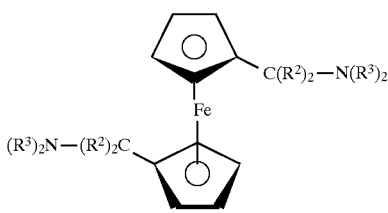

in which the radicals $R^2$ and $R^3$ are as defined in claim 1, to asymmetric mono-ortho-lithiation using n-butyllithium in the presence of a homochiral tertiary amine, and reacting the chiral monolithium compound in-situ with a chlorophosphine of the formula $ClP(R^1)_2$ in which the radicals $R^1$ are as defined in claim 1.

7. A process for preparing an optically active $C_2$-symmetric diphosphine of the formula I as claimed in claim 1, in which the radicals $R^1$, $R^2$ and $R^3$ are as defined in claim 1 and X is $P(R^1)_2$, which comprises subjecting an optically active monophosphine of the formula I in which the radicals $R^1$, $R^2$ and $R^3$ are as defined in claim 1 and X is hydrogen to asymmetric mono-ortho-lithiation with n-butyllithium in the presence of a homochiral tertiary amine, and reacting the chiral monolithium compound in-situ with a chlorophosphine of the formula $ClP(R^1)_2$ in which the radicals $R^1$ are as defined in claim 1.

8. A process for preparing an optically active $C_2$-symmetric diphosphine of the formula I as claimed in claim 1, in which the radicals $R^1$, $R^2$ and $R^3$ are as defined in claim 1 and X is $P(R^1)_2$, which comprises subjecting a compound of the formula III

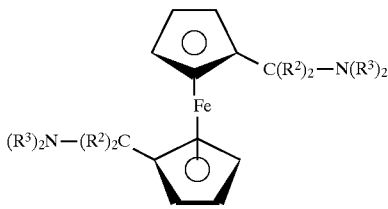

in which $R^2$ and $R^3$ are as defined in claim 1 first of all to deprotonation with n-butyllithium in the presence of a homochiral tertiary amine, then to phosphinylation by adding a chlorophosphine of formula $ClP(R^1)_2$ in which $R^1$ is as defined in claim 1, then carrying out the second deprotonation step by renewed addition of n-butyllithium, without isolating the monophosphine formed, and, finally, bringing about the second phosphinylation by renewed addition of the chlorophosphine of the formula $ClP(R^1)_2$.

9. A process for preparing a racemic compound of the formula I as claimed in claim 1, in which $R^1$, $R^2$, $R^3$ and X are as defined in claim 1, which comprises subjecting an achiral ferrocene of the formula III

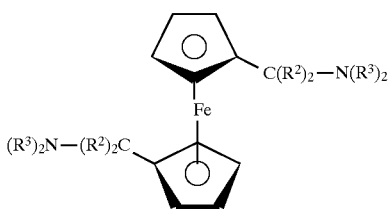

in which
the radicals $R^2$ and $R^3$ are as defined in claim 1, or a racemic monophosphine of the formula I in which $R^1$, $R^2$ and $R^3$ are as defined in claim 1 and X is hydrogen, to symmetric mono-ortho-lithiation with n-butyllithium in the presence of a racemic or achiral tertiary amine, and reacting the monolithium compound in-situ with a chlorophosphine of the formula $ClP(R^1)_2$ in which the radicals $R^1$ are as defined in claim 1 or, in the case of the preparation of a diphosphine from a compound of the formula III, carrying out stepwise symmetric dilithiation/diphosphinylation.

10. A process as claimed in claim 9, wherein the amine employed is N,N,N',N'-tetramethylethylenediamine.

11. A method of using the compound of the formula I as claimed in claim 1 as a ligand in transition metal complexes.

12. A transition metal complex comprising at least one ligand of the formula I as claimed in claim 1.

13. A complex of a compound of the formula I as claimed in claim 1 with the transition metal ruthenium, rhodium, iridium, nickel, palladium, platinum or silver.

14. A method of using the transition metal complex as claimed in claim 12 as a catalyst.

15. A method of using the transition metal complex as claimed in claim 12 for asymmetric catalysis.

16. A method of using the transition metal complex as claimed in claim 13 for asymmetric catalysis.

17. A compound of the formula II

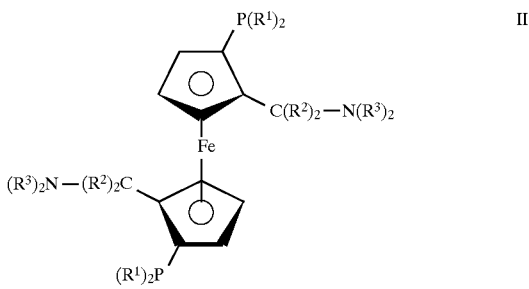

in which the substituents $R^1$ are cyclohexyl, unsubstituted phenyl $C_6H_5$ or substituted phenyl $C_6H_{5-n}R^4_n$, where n is 1 to 5 and the substituents $R^4$ are unbranched or branched $C_1$- to $C_4$-alkyl, $C_1$- to $C_4$-alkoxy or halogen;

the two geminal substituents $R^2$ together are a doubly bonded oxygen atom (i.e. $(R^2)_2$ is $=O$) or each substituent $R^2$ on its own is hydrogen;

the substituents $R^3$, each on their own, are unbranched or branched $C_1$- to $C_4$-alkyl, cyclopentyl, cyclohexyl, unsubstituted phenyl $C_6H_5$ or substituted phenyl $C_6H_{5-n}R^4_n$, where n and $R^4$ are as defined above under $R^1$, or the substituents $R^3$ are connected to one another to form a ring, in which case together they are tetramethylene $-(CH_2)_4-$, pentamethylene $-(CH_2)_5-$, 3-oxapentamethylene $-(CH_2)_2-O-(CH_2)_2-$ or N-methyl-3-azapentamethylene $-(CH_2)_2-N(CH_3)-(CH_2)_2-$;

or a salt thereof.

18. A process for preparing a compound of the formula II in which the radicals $R^1$, $R^2$ and $R^3$ are as defined in claim 17, which comprises subjecting a compound of the formula III

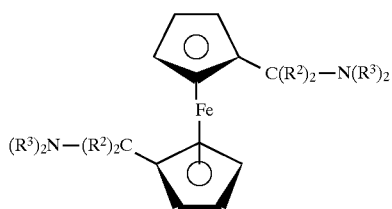

in which
the radicals $R^2$ and $R^3$ are as defined in claim 17 to ortho-lithiation with sec-butyllithium in the presence of a tertiary amine, and reacting the dilithium compound in-situ with a chlorophosphine of the formula $ClP(R^1)_2$ in which the radicals $R^1$ are as defined in claim 17.

19. A process as claimed in claim 18, wherein the amine employed is N,N,N',N'-tetramethylethylenediamine.

20. A method of using the compound of the formula II as claimed in claim 17 as a ligand in transition metal complexes.

21. A transition metal complex comprising at least one ligand of the formula II as claimed in claim 17.

22. A method of using the transition metal complex as claimed in claim 21 as a catalyst.

* * * * *

UNITED STATES PATENT AND TRADEMARK OFFICE
CERTIFICATE OF CORRECTION

PATENT NO. : 5,856,540
DATED : January 5, 1999
INVENTOR(S) : Jendralla

It is certified that error appears in the above-identified patent and that said Letters Patent is hereby corrected as shown below:

Column 1
    Title Page, Item [54], in the Title, line 1, "2,2'-DISUBTITUTED"
        should read --2,2'-DISUBSTITUTED--.

*Title Page, Item [57], in the Abstract, line 13, in formula II, "$C(R')_2 - N(R^3)_2$"
        should read --$C(R^2)_2 - N(R^3)_2$--.

Claim 3, col. 32, line 55, "R", should read --$R^2$--.

Signed and Sealed this

Sixteenth Day of November, 1999

Attest:

Q. TODD DICKINSON

*Attesting Officer*   *Acting Commissioner of Patents and Trademarks*